US012318377B2

(12) United States Patent
Kovarik et al.

(10) Patent No.: US 12,318,377 B2
(45) Date of Patent: *Jun. 3, 2025

(54) METHOD AND SYSTEM FOR REDUCING THE LIKELIHOOD OF A PORPHYROMONAS GINGIVALIS INFECTION IN A HUMAN BEING

(71) Applicant: Seed Health, Inc., Venice, CA (US)

(72) Inventors: Katherine Rose Kovarik, Englewood, CO (US); Joseph E. Kovarik, Englewood, CO (US)

(73) Assignee: Seed Health, Inc., Venice (CA)

( * ) Notice: Subject to any disclaimer, the term of this patent is extended or adjusted under 35 U.S.C. 154(b) by 745 days.

This patent is subject to a terminal disclaimer.

(21) Appl. No.: 17/543,992

(22) Filed: Dec. 7, 2021

(65) Prior Publication Data

US 2022/0088001 A1 Mar. 24, 2022

Related U.S. Application Data

(63) Continuation-in-part of application No. 16/804,361, filed on Feb. 28, 2020, now Pat. No. 11,191,665, which is a continuation-in-part of application No. 16/020,433, filed on Jun. 27, 2018, now Pat. No. 10,583,033, which is a continuation-in-part of application No. 15/342,642, filed on Nov. 3, 2016, now Pat. No. 10,010,568, application No. 17/543,992 is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, application No. 17/543,992 is a continuation-in-part of application No. 15/228,454, filed on Aug. 4, 2016, now Pat. No. 9,585,920, and a continuation-in-part of application No. 14/752,192, filed on Jun. 26, 2015, now Pat. No. 9,549,842, application No. 17/543,992 is a continuation-in-part of application No. 16/884,772, filed on May 27, 2020, and a continuation-in-part of application No. 16/904,056, filed on Jun. 17, 2020.

(60) Provisional application No. 62/260,906, filed on Nov. 30, 2015, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013.

(51) Int. Cl.
*A61K 31/4704* (2006.01)
*A61K 9/68* (2006.01)
*A61K 31/4164* (2006.01)
*A61K 31/546* (2006.01)
*A61K 47/26* (2006.01)

(52) U.S. Cl.
CPC ........ *A61K 31/4704* (2013.01); *A61K 9/0058* (2013.01); *A61K 31/4164* (2013.01); *A61K 31/546* (2013.01); *A61K 47/26* (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 4,568,639 A | 2/1986 | Lew |
| 4,687,841 A | 8/1987 | Spilburg et al. |
| 4,720,486 A | 1/1988 | Spilburg et al. |
| 4,995,555 A | 2/1991 | Woodruff |
| 5,277,877 A | 1/1994 | Jeffrey et al. |
| 5,614,501 A | 3/1997 | Richards |
| 6,287,610 B1 | 9/2001 | Bowling et al. |
| 6,514,484 B2 | 2/2003 | Rajaiah |
| 6,569,474 B2 | 5/2003 | Clayton et al. |

(Continued)

FOREIGN PATENT DOCUMENTS

| | | |
|---|---|---|
| WO | WO 2011/020780 | 2/2011 |
| WO | WO 2011/029701 | 5/2013 |

(Continued)

OTHER PUBLICATIONS

U.S. Appl. No. 11/083,760, filed Aug. 10, 2021, Han.

(Continued)

*Primary Examiner* — Brian Gangle
(74) *Attorney, Agent, or Firm* — Sheridan Ross P.C.

(57) ABSTRACT

A method and system of reducing the likelihood of a Porphyrmonas gingivalis infection in a human being includes the use of an anti-biofilm agent, compounds that facilitate the growth of desired bacteria beneficial to a person's health, and compositions that reduce the growth of Porphyrmonas gingivalis bacteria, thereby reducing the virulence factor gingipain. In other embodiments, the likelihood that a subject will suffer from neurodegenerative diseases, such as Alzheimer's Disease, is reduced by administering, via local gingival application to a subject that has been diagnosed with periodontitis, an effective amount of a composition to reduce Porphyrmonas gingivalis bacteria residing on the subgingival tooth area of the subject. Methods involve the targeting of the microbiome of an individual to promote health and to treat inflammatory diseases, including specifically neurodegenerative diseases, by the modification of an individual's oral microbiome and effective management of oral health care.

20 Claims, 6 Drawing Sheets

(56) References Cited

U.S. PATENT DOCUMENTS

| | | |
|---|---|---|
| 6,722,577 B2 | 4/2004 | Dobyns, III |
| 7,267,975 B2 | 9/2007 | Strobel et al. |
| 7,353,194 B1 | 4/2008 | Kerker et al. |
| 7,540,432 B2 | 6/2009 | Majerowski et al. |
| 7,820,420 B2 | 10/2010 | Whitlock |
| 7,862,808 B2 | 1/2011 | Isolauri et al. |
| 8,034,606 B2 | 10/2011 | Park et al. |
| 8,197,872 B2 | 6/2012 | Mills et al. |
| 8,349,313 B2 | 1/2013 | Smith et al. |
| 8,420,074 B2 | 4/2013 | Rehberger et al. |
| 8,454,729 B2 | 6/2013 | Mittelmark et al. |
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,758,764 B2 | 6/2014 | Masignani et al. |
| 8,815,538 B2 | 8/2014 | Lanzalaco et al. |
| 8,945,839 B2 | 2/2015 | Zhang |
| 8,951,775 B2 | 2/2015 | Castiel |
| 9,011,834 B1 | 4/2015 | McKenzie et al. |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 10,010,568 B2 | 7/2018 | Kovarik et al. |
| 10,583,033 B2 | 3/2020 | Kovarik |
| 10,730,826 B2 | 8/2020 | Konradi et al. |
| 11,191,665 B2 | 12/2021 | Kovarik |
| 2003/0083287 A1 | 5/2003 | Burgess et al. |
| 2003/0206995 A1 | 11/2003 | Bowling et al. |
| 2004/0053352 A1 | 3/2004 | Ouyang et al. |
| 2004/0115223 A1 | 6/2004 | Follansbee |
| 2004/0142463 A1 | 7/2004 | Walker et al. |
| 2004/0166501 A1 | 8/2004 | Azimzai et al. |
| 2005/0118655 A1 | 6/2005 | Weinstock et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0207955 A1 | 9/2007 | Tanihara et al. |
| 2007/0231923 A1 | 10/2007 | Cumberland et al. |
| 2008/0112983 A1 | 5/2008 | Bufe et al. |
| 2008/0305089 A1 | 12/2008 | Bufe et al. |
| 2009/0205083 A1 | 8/2009 | Gupta et al. |
| 2010/0029832 A1 | 2/2010 | Pinnavaia et al. |
| 2010/0260720 A1 | 10/2010 | Sprenger |
| 2012/0027786 A1 | 2/2012 | Gupta |
| 2012/0029832 A1 | 2/2012 | Dodgson |
| 2012/0039806 A1 | 2/2012 | Lahoud et al. |
| 2012/0128597 A1 | 5/2012 | Peters et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0236488 A1 | 9/2013 | Dashper et al. |
| 2013/0259834 A1 | 10/2013 | Klaenhammer et al. |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0238411 A1 | 8/2014 | Kovarik |
| 2014/0255351 A1 | 9/2014 | Berstad et al. |
| 2014/0349405 A1 | 11/2014 | Sontheimer et al. |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0045546 A1 | 2/2015 | Siksnys et al. |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0166641 A1 | 6/2015 | Goodman |
| 2015/0190435 A1 | 7/2015 | Henn et al. |
| 2015/0216917 A1 | 8/2015 | Jones |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0151427 A1 | 6/2016 | Whitlock et al. |
| 2016/0168594 A1 | 6/2016 | Zhang et al. |
| 2016/0199424 A1 | 7/2016 | Berry et al. |
| 2016/0206666 A1 | 7/2016 | Falb et al. |
| 2016/0271189 A1 | 9/2016 | Cutcliffe |
| 2016/0314281 A1 | 10/2016 | Apte |
| 2017/0042860 A1 | 2/2017 | Kashyap et al. |
| 2017/0246269 A1 | 8/2017 | Hajishengallis et al. |
| 2018/0110795 A1 | 4/2018 | Frias-Lopez |
| 2019/0315642 A1 | 10/2019 | Parsley et al. |
| 2020/0148642 A1 | 5/2020 | Konradi et al. |
| 2021/0169954 A1 | 6/2021 | Balani et al. |
| 2021/0308028 A1 | 10/2021 | Yang et al. |
| 2021/0321756 A1 | 10/2021 | McLaughlin |

FOREIGN PATENT DOCUMENTS

| | | |
|---|---|---|
| WO | WO 2013/107750 | 7/2013 |
| WO | WO 2014/182632 | 5/2014 |

OTHER PUBLICATIONS

Ran et al., 2013 (Genome engineering using CRISPR-Cas9 system, Nature Protocols 8(11); 221-2308) (Year 2013).

Johnston et al. 2017 (Restriction-modification mediated barriers to exogenous DNA uptake and incorporation employed by Prevotella intermedia; PLOS one 12(9): e0185234) (Year: 2017).

Fentahun et al., 2012 (Leptospirosis and its Public Health Significance: A Review; European Journal of Applied Sciences 4(6): 238-244) (Year: 2012).

Steere et al. 2006 (Therapy for Lyme Arthritis: Strategies for the Treatment of Antibiotic-Refractory Arthritis, Arthritis and Rheumatism 54(10: 3079-3086) (Year: 2006).

Kamer et al. 2008 (Alzheimer's Disease and Peripheral Infections: The Possible Contribution from Periodontal Infections, Model and Hypothesis; Journal of Alzheimer's Disease 13: 437-449).

Deasy et al. 1989 (Use of strips containing tetracycline hydrochloride or metronidazole for the treatment of advanced periodontal diseases; J. Pharm. Pharmacol. 41.

Schwach-Abdellaoui et al. 2000 (Local delivery of antimicrobial agents for the treatment of periodontal diseases; European Journal of Pharmaceutics and Biopharmaceutics; 50: 83-89).

Bromberg et al. 2001 (Novel periodontal drug delivery system for treatment of periodontitis; Journal of Controlled Release; 71: 251-259).

Miklossy J. (1994) Alzheimer Disease—A Spirochetosis? In: Giacobini E., Becker R.E. (eds) Alzheimer Disease. Advances in Alzheimer Disease Therapy. Birkhäuser Boston.

Miklossy J. (2011) Alzheimer's disease—a neurospirochetosis. Analysis of the evidence following Koch's and Hill's criteria, Journal of Neuroinflammation, 2011 8:90.

Miklossy, J. (2016) Microbes and Alzheimer's Disease J Alzheimers Dis. 2016; 51(4): 979-984.

(56) References Cited

OTHER PUBLICATIONS

Allen, Herbert, B. (2016) Alzheimer's Disease: Assessing the Role of Spirochetes, Biofilms, the Immune System, and Amyloid-β with Regard to Potential Treatment and Prevention, Journal of Alzheimer's Disease, vol. 53, No. 4, pp. 1271-1276.
Allen, et. al. (2018) Bioethical Challenges Arising from the Microbiology and Pathology of Alzheimer's, Current Neurobiology.

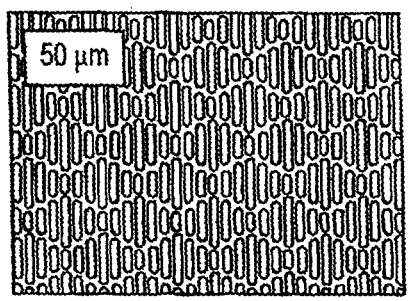
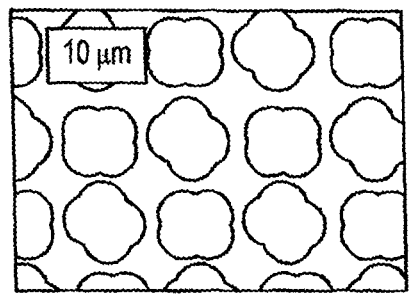
FIG.2a　　　　　　　　FIG.2b
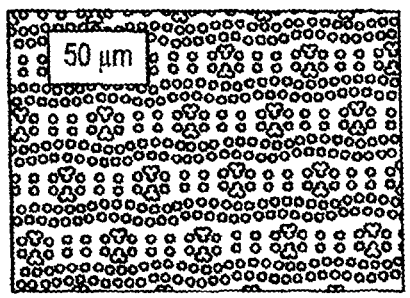
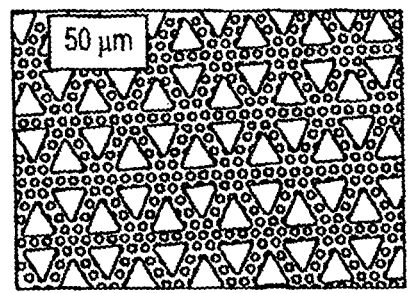
FIG.2c　　　　　　　　FIG.2d

METHOD AND SYSTEM FOR REDUCING THE LIKELIHOOD OF A PORPHYROMONAS GINGIVALIS INFECTION IN A HUMAN BEING

RELATED APPLICATIONS

The present application is a continuation-in-part of U.S. patent application Ser. No. 16/804,361, filed Feb. 28, 2020 (now U.S. Pat. No. 11,191,665, issued Dec. 7, 2021), which is a continuation-in-part of U.S. patent application Ser. No. 16/020,433, filed Jun. 27, 2018 (now U.S. Pat. No. 10,583,033, issued Mar. 10, 2020), which is a continuation-in-part application of U.S. Ser. No. 15/342,642, filed Nov. 3, 2016 (now U.S. Pat. No. 10,010,568, issued Jul. 3, 2018), which seeks priority from U.S. Provisional Patent Application Ser. No. 62/260,906, filed Nov. 30, 2015.

The present application is a continuation-in-part of U.S. Ser. No. 15/270,034, filed Sep. 20, 2016 (now U.S. Pat. No. 9,750,802, issued Sep. 5, 2017), which is a continuation-in-part of U.S. patent application Ser. No. 14/954,074, filed Nov. 30, 2015 (now U.S. Pat. No. 9,457,077, issued Oct. 4, 2016), which is a continuation-in-part of U.S. patent application Ser. No. 14/574,517, filed Dec. 18, 2014, (now U.S. Pat. No. 9,408,880, issued Aug. 9, 2016), which claims priority from U.S. Provisional Patent Application Ser. No. 62/072,476, filed on Oct. 30, 2014, U.S. Provisional Patent Application Ser. No. 62/053,926, filed Sep. 23, 2014, U.S. Provisional Patent Application Ser. No. 62/014,855, filed Jun. 20, 2014 and U.S. Provisional Patent Application Ser. No. 61/919,297, filed on Dec. 20, 2013.

The present application also is a continuation-in-part of U.S. patent application Ser. No. 15/228,454, filed Aug. 4, 2016 (now U.S. Pat. No. 9,585,920, issued Mar. 7, 2017).

This application is also a continuation-in-part of U.S. patent application Ser. No. 14/752,192 filed on Jun. 26, 2015 (now U.S. Pat. No. 9,549,842, issued Jan. 24, 2017) which is a continuation-in-part of U.S. patent application Ser. No. 14/225,503, filed on Mar. 26, 2014, (now U.S. Pat. No. 9,445,936, issued Sep. 20, 2016) which is a continuation of U.S. patent application Ser. No. 13/367,052, filed on Feb. 6, 2012 (now U.S. Pat. No. 8,701,671, issued on Apr. 22, 2014), and claims priority from U.S. Provisional Patent Application Ser. No. 61/556,023 filed Nov. 4, 2011 and U.S. Provisional Patent Application Ser. No. 61/439,652 filed on Feb. 4, 2011.

This application is also a continuation-in-part of U.S. patent application Ser. No. 16/884,772 filed on May 27, 2020.

This application is also a continuation-in-part of U.S. patent application Ser. No. 16/904,056, filed on Jun. 17, 2020.

The entire disclosure of the prior applications are considered to be part of the disclosure of the accompanying application and are hereby incorporated by reference.

FIELD OF THE INVENTION

The present invention, in various embodiments, is directed to the targeting of the microbiome of an individual to promote health and to treat inflammatory diseases, including specifically Alzheimer's disease, by the modification of an individual's oral microbiome and effective management of oral health care. The cause of the vast majority of Alzheimer's Disease (AD) is submitted to be periodontitis, and thus, AD is both treatable and preventable by targeting the oral microbiome to prevent later infection of brain tissue by oral spirochetes.

BACKGROUND OF THE INVENTION

Alzheimer's disease (AD) is a neurodegenerative disease which significantly increases with age. Currently there is no cure for Alzheimer's disease and ultimately it results in death. It is estimated that in 2014, there were 5.2 million Americans living with Alzheimer's disease, two thirds consisting of women. One in six women are estimated to be at risk for developing Alzheimer's. Alzheimer's disease is the 6th leading cause of death in the United States, and approximately 500,000 people die each year from the disease. It is the most expensive condition in the U.S. to treat, with the direct cost to the U.S. of caring for those with Alzheimer's exceeding $200 billion, including $150 billion in costs to Medicare and Medicaid. It is estimated that these costs will reach $1.2 trillion in 2050, as it is expected that 16 million Americans will be living with Alzheimer's disease at that time.

Alzheimer's disease was first described by the Bavarian psychiatrist Alois Alzheimer in 1907. It is a progressive neuropsychiatric disorder which begins with short term memory loss and proceeds to loss of cognitive functions, disorientation, impairment of judgment and reasoning and, ultimately, dementia. AD is the most common form of dementia. There is currently no treatment for AD that can reverse or slow down the disease progression. AD represents a major health problem and an effective treatment of the disease would represent a major breakthrough.

The clinical manifestations of Alzheimer's disease begin with subtle short-term memory deficits and depressive symptoms, followed by orientation and language difficulties. Intellectual functions progressively disappear and patients become entirely dependent, typically surviving in this devastating state for more than a decade. Death generally occurs from a secondary infection, frequently from pneumonia or urinary infection. The duration of the disease from the appearance of the first symptoms and the manifestation of dementia varies between 5 and 20 years. Clinical diagnosis of Alzheimer's disease often occurs long after the onset of the disease. It is usually first noticed by immediate family members who detect problems with short-term memory and unusual behavior. Confirmation is achieved post-mortem by detecting the presence of the pathological hallmarks of the disease, amyloid plaques and neurofibrillary tangles.

The mainstream current FDA-approved pharmacological treatment for Alzheimer's disease is to ameliorate cognitive decline by restoring neurotransmitter signaling between neurons. Four of the five medications approved by the FDA for prescription to Alzheimer's disease patients are aimed at increasing extracellular levels of acetylcholine by delaying its degradation (the acetylcholinesterase inhibitors: tacrine, rivastigmine, galantamine and donepezil). The fifth approved drug is memantine, a partial antagonist for the ionotropic glutamate NMDA receptor. Memantine presumably reduces calcium-mediated glutamate excitotoxicity, hence slowing synaptic and neuronal loss characteristically observed in the Alzheimer's diseased brain. Although these treatments have proven to maintain cognitive function in Alzheimer's diseased patients, the therapeutic effect is transient and primarily symptomatic. These treatments are not mechanism-based and do not seem to have any disease-modifying effects. Moreover, no significant proof supports that these drugs play a role in the prevention of cognitive decline or the reversal of pathological hallmarks and neurodegeneration in Alzheimer's disease.

"The causes of Alzheimer's disease remain unknown and there is no cure." August 2014 issue of the Journal of Alzheimer's Disease. Previous suggestions that particular genetic factors were involved in Alzheimer's disease, e.g. the E4 allele, and associations of APOE and the disease, have been shown to be incorrect, as there is no evidence for linkage between Alzheimer's disease and APOE.

There is, as yet, no cure for Alzheimer's disease despite concerted efforts and investment by industry. There is therefore a long-felt but unsolved need for a method and system to prevent Alzheimer's disease in order to spare tens of millions of individuals the terrible fate otherwise awaiting them.

SUMMARY OF THE INVENTION

The present invention provides a method and system for reducing the likelihood that one will suffer from Alzheimer's disease and thus, preventing Alzheimer's disease in a manner that deals with the causative agents of the disease. The present invention is focused on steps that can be taken decades in advance of the symptoms of Alzheimer's disease first appearing. For the first time, the present invention provides a way for individuals to adopt positive behaviors, techniques and use compositions and products that can thwart the progression of Alzheimer's disease. The present invention is directed, from a more general perspective, on the human microbiome and its relationship to inflammatory responses related to chronic diseases that have, to date, been unresolved and misunderstood. The relationship between the oral microbiome and Alzheimer's disease is focused on to determine an effective method and system to prevent the initiation and the progression of the disease.

Humans have co-evolved with micro-organisms and have a symbiotic or mutualistic relationship with their resident microbiomes. As at other body surfaces, the mouth has a diverse microbiota that grows on oral surfaces as structurally and functionally organized biofilms. On occasions, the oral microbiota breaks down, and previously minor components of the microbiota outcompete beneficial bacteria, thereby increasing the risk of disease.

There is increasing evidence that the reach of gut and oral microbes extends beyond the intestine, affecting systemic processes, such as metabolism and organ functions of the brain, the cardiovascular system, liver, and other organs. Several metabolomic studies have identified hundreds of compounds in blood that are specifically derived or dependent on the presence of gut microbes.

Researchers have analyzed people's gut bacteria by their occupation and have found that those who had regular contact with livestock, such as farmers and their wives, had bacterial communities dominated by *Prevotella*, a type of bacteria that is also abundant in the gut microbiota of cattle and sheep. The anaerobic black-pigmented *Prevotella intermedia* is a Gram-negative rod-shaped bacterium whose habitat is the strictly anaerobic environments of the gastrointestinal tract and gingival crevice. *P. intermedia* plays an important role in the onset and subsequent development of polymicrobial periodontal diseases. It is known that *Prevotella intermedia* adaptation to oxidative stress influences the virulence of the microorganism.

One aspect to the mystery of Alzheimer's disease etiopathogenesis lies in the relative absence of Alzheimer's disease in certain Amish communities. The prevalence of *Prevotella* in the oral cavity of the Amish, the production of nitric oxide by this bacteria, and the reduction of spirochetes in the brains of the Amish, all present evidence as to an effective avenue for therapeutic intervention in Alzheimer's disease prevention and/or progression. The insights gained from an evaluation of the Amish, especially with respect to the oral microbiome they possess and the absence of various diseases they suffer from, is one of the foundational aspects of various embodiments of the present invention. In some embodiments, mimicking particular conditions of the Amish is accomplished to achieve some of the benefits derived from the oral microbiome established in certain Amish populations.

One aspect of the present invention is also directed to the pathology of Alzheimer's disease as it relates to inflammation. Reactive microglia and astrocytes adjacent to Aβ plaques is a common observation in the brain of Alzheimer's disease sufferers. It is thought that activated glia is at first beneficial for degrading Aβ plaques. Chronic inflammation, however, leads to the production of several cytokines that have been demonstrated to exacerbate other Alzheimer's disease pathologies. An increased infectious burden and higher serum levels of inflammatory cytokines have been associated with serum Aβ markers in Alzheimer's disease patients. Chronic infections caused by these pathogens have been shown to result in cardio-cerebral vascular disorders, which subsequently promote the development of Alzheimer's disease. These studies provide supporting evidence that accumulative infections are associated with Alzheimer's disease and supports the role of infection and inflammation in the etiopathogenesis of Alzheimer's disease. Certain aspects of the present invention are directed to a reduction in the risk of Alzheimer's disease through a combination of antibiotic and anti-inflammatory therapy.

The fact that Alzheimer's disease usually develops in later life suggested that a slow-acting unconventional infectious agent acquired at an early age and requiring decades to become active may be involved in its etiology. Oral spirochetes are such unconventional infectious agents. Spirochetes have been found in about 90% of Alzheimer's patients, while these bacteria were virtually absent in the brains of healthy age-matched controls. Once a spirochete infection begins in the brain, it causes disease by having plaques or masses formed along the cerebral cortex. It is believed that such plaque formation is a normal immune response to an invasive bacteria in the brain tissue. ARP is the main component of amyloid plaques and is instrumental in the pathogenesis of Alzheimer's disease. In Alzheimer's disease, the brain's normal defenses become dysfunctional as the macrophages (microglia) become trapped and then attacked within the core of the spirochete plaque. With immune dysfunction setting in, the spirochete infection intensifies involving more and more brain cells. Damaged brain cells produce amyloid-beta protein as an adaptive response to the infection. As an adaptive response to infectious organisms, like invading spirochetes, amyloid-beta protein is produced, which we now know has anti-bacterial properties. Amyloid-beta deposits grow and begin to affect brain cell connections and communication highways. With damaged connections and communication highways, dementia symptoms begin and gradually worsen.

Spirochetes are a commonly isolated microorganism in moderate to severe periodontitis, suggesting that periodontopathic bacteria can invade the brain by systemic circulation as well as via peripheral nerve pathways. The presence of oral bacteria in systemic circulation is usually expected when heavy bacterial plaques are present.

Alzheimer's disease is characterized by salient inflammatory features, microglial activation, and increased levels of proinflammatory cytokines which contribute to the inflammatory status of the central nervous system. The present inventors believe that, like other spirochetes based diseases, treatment decades in advance of the appearance of symptoms is at the heart of addressing Alzheimer's disease. For example, in various ways, Alzheimer's disease shares certain similarities with syphilis. Treponema pallidum (*T. pallidum*) persists in the syphilitic brain, which sustains chronic infection and inflammation, forms amyloid plaques and causes slowly progressive dementia. Dementia develops years or decades following the primary syphilitic infection. Historic observations and illustrations published in the first half of the 20th Century indeed confirm that the pathological hallmarks, which define Alzheimer's disease are also present in syphilitic dementia. Cortical spirochetal colonies are made up of innumerable tightly spiraled *Treponema pallidum* spirochetes, which are morphologically indistinguishable from senile plaques using conventional light microscopy. Local brain amyloidosis also occurs in general paresis and, as in Alzheimer's disease, corresponds to amyloid beta. Thus, chronic spirochetal infections can cause dementia and support a causal relationship between various spirochetal infections and Alzheimer's disease. They also indicate that local invasion of the brain by these helically shaped bacteria reproduce the filamentous pathology characteristic of Alzheimer's disease. Chronic infection by spirochetes, and co-infection with other bacteria, is therefore involved in the etiology of Alzheimer's disease. Addressing this infection progression is one aspect of the present invention, and one focus is therefore on preventing spirochetes bacteria from growing in the oral cavity and in reducing the ability of such spirochetes to travel through the blood or via the nervous system to regions of the brain.

The similarities of the clinical and pathological manifestations of syphilis and Lyme disease are well documented. Lyme disease, like Alzheimer's disease, involves the creation of plaques in brain tissue. Thus, one aspect of the present invention is to adopt a similar treatment regimen with respect to Alzheimer's disease as has been found to be effective to combat syphilis and Lyme disease. Syphilis is easy to treat with penicillin, one of the most widely used antibiotics. People who are allergic to penicillin may be treated with a different oral antibiotic, such as doxycycline, azithromycin, or ceftriaxone. Like syphilis, however, the damage already done by Alzheimer's disease cannot be reversed. It is thus imperative that early diagnosis, e.g. of periodontitis, be followed up with an appropriate treatment plan to avoid the dire consequences of Alzheimer's disease progression.

There is compelling evidence that treponemes, spiral-shaped bacteria, are involved in the etiology of several chronic diseases, including chronic periodontitis. Treponemes are members of the normal oral microbiota of healthy individuals, albeit in very low numbers. Treponemes are members of the Spirochaetes phylum, a clade now believed to be distinct from both Gram-positive and Gram-negative bacteria, that is believed to have undergone extensive horizontal gene transfer with Archae and possibly with eukaryotic organisms. Chronic periodontitis is a polymicrobial disease, and co-infection of *Treponema denticola* with other periodontal pathogens can enhance alveolar bone resorption. The bacterium has a suite of molecular determinants that enable it to cause tissue damage and subvert the host immune response. The human oral cavity harbors more than 60 different *Treponema* species, previously considered to be commensal spirochetes, but now revealed to be predominant and invasive periodontal pathogens. Spirochetes frequently co-infect with other bacteria and viruses.

When considering the virulence characteristics of spirochetes, and in particular, *T. denticola*, it is imperative to understand that it is part of a pathogenic bacterial consortium, and its interactions with other bacterial species are important for disease pathology. The bacterial composition of subgingival plaque in individuals with chronic periodontitis often find *P. gingivalis* and *T. denticola* and *T. forsythia* together.

Uncontrolled inflammation of the periodontal area may arise when complex microbial communities transition from a commensal to a pathogenic entity. Communication among constituent species leads to polymicrobial synergy between metabolically compatible organisms that acquire functional specialization within the developing community. Keystone pathogens, even at low abundance, elevate community virulence, and the resulting dysbiotic community targets specific aspects of host immunity to further disable immune surveillance while promoting an overall inflammatory response. Inflammophilic organisms benefit from proteinaceous substrates derived from inflammatory tissue breakdown. Inflammation and dysbiosis reinforce each other, and the escalating environmental changes further select for a pathobiotic community.

There is a long felt but unsolved need for an answer to the Alzheimer's disease quandary. Without understanding the cause of the disease, however, attempts to simply combat symptoms are ill advised and potentially dangerous. The treatment for AD may not be a blockbuster drug that will entice large pharmaceutical companies. A silver bullet for AD may therefore not be in the cards. Rather, as AD is a disease that is slow to progress due to its origins in an individual's oral microbiome and later progression to brain tissue, its treatment and prevention, as described herein, is achieved via methods and systems that are directed to improving the oral microbiome health, in the prevention of the occurrences that lead to the spread of oral bacteria to an individual's brain, and in the ongoing maintenance of oral health via use of novel oral strips that provide and/or nurture an environment where beneficial bacteria can thrive and where spirochetes growth can be controlled. Regular dental practices must be reviewed and adapted to prevent the occasions where harmful bacteria can reach a person's bloodstream, and protective measures are warranted in such circumstances, followed by establishment of better oral microbiome conditions to thwart the progression of AD. Lessons from the Amish can be gleaned from their oral microbiome which appears to protect them from many of the ravages of modern diseases.

In particular embodiments, addressing an individual's oral health in a manner directly related to brain health is achieved by various methods, including the purposeful exposure of an individual with bacteria of the genus *Prevotella* to decrease the incidence of periodontitis, and the provision of oral strips having antibacterial characteristics, etc. to reduce the likelihood of Alzheimer's Disease. Bacteria from the oral cavity can weaken the blood brain barrier, enter the brain, and accelerate the events leading to cognitive decline and Alzheimer's disease. The present inventors submit that maintaining the health of the oral cavity offers an incalculable potential return on investment.

Various aspects of the present invention are directed to a method of reducing the likelihood of an inflammatory disease, and in particular AD, developing in a subject, with such method including the provision of a particularly designed bioadhesive strip to a subject that has been diagnosed with periodontitis. Suitable strips are adapted for oral cavity application and have a first and second side, with the first side having a bioadhesive that is adapted to bind to a portion of an individual's oral cavity, and in particular either to dental surfaces or a mucosal membrane for an extended period of time, e.g. for at least 1 hour, more preferably more than 3 hours, and in some scenarios, for at least twelve hours or more, while inside a person's mouth. The second side preferably has a specially textured surface that has an anti-microbial characteristic derived from its surface topography, such topography resisting bioadhesion of undesired bacteria that are typically present in a human's mouth. Moreover, as spirochetes employ copper and manganese for growth, the strip is preferably devoid of manganese and copper. Conversely, because zinc is important to many beneficial oral bacteria, such strips preferably include zinc components therein. As described herein the use of a strip that has on its surface a pattern defined by a plurality of spaced apart features each having at least one microscale dimension and having at least one neighboring feature having a substantially different geometry, is useful in that such a micro-surface design thwarts the growth of bacteria on its surface. Use of such anti-bacterial textured surfaces is therefore important in the maintenance of desired oral bacterial populations and in the ability, especially without the use of antibiotics, to reduce the growth of undesired bacteria, especially those associated with periodontitis. Such strips can also or alternately include various mineral (e.g. zinc) and anti-biotic components, such a variety of antibiotics that preferably target undesired bacteria believed to be involved in the progression of periodontitis. As the formation of biofilms is believed instrumental in the ability of certain bacteria to avoid antibiotic contact, e.g. spirochetes, the use of agents that assist in breaking down biofilms are important constituents of various embodiments of the present invention. Thus, as one of skill in the art will appreciate, a variety of anti-biofilm agents can be included in the oral strips as described herein, that may rely upon a variety of anti-adhesion-mediated mechanisms. For example, curcumin, enzymes, like DNase I, α-amylase and DspB, serrapeptase, etc can be employed.

Certain preferred embodiments include administering to the oral cavity of a subject an effective amount of *Prevotella intermedia*, even more preferably *Prevotella intermedia* modified using CRISPR-Cas or CRISPR-Cpf1 to remove at least one virulence factor. It is believed that maintaining *Prevotella* bacteria in the oral microbiome, but having a strain that lacks particular virulence factors, such as those associated with biofilm formation, provides benefits in that the native ability of such bacteria to produce NO is preserved, thus facilitating the retention of positive attributes while deleting undesired characteristics of the bacteria. While *Prevotella* is one preferred species of bacteria that is believed useful in modifying in this regard, one of skill in the art will appreciate the various other bacteria that reside in a person's oral microbiome that can also be modified to generate and foster a microbiome that is more conducive to treatments with anti-biofilm formation, that permits the use of various antibiotics as described herein, and in establishing a better microbiome environment such that spirochetes growth and infection can be addressed. The use of the oral strips as described herein as both a way to administer anti-bacterial substances and anti-biofilm agents, may also be employed to deliver desired amounts of desired bacteria, such as modified *Prevotella*, thus ensuring that such modified bacteria are placed in a desired portion of one's oral cavity to achieve maximum effect.

Methods of the present invention further include orally administering to the subgingival tooth area of the subject an effective amount of an antibiotic effective to kill spirochetes bacteria residing on the subgingival tooth area of the subject. Preferably the antibiotic comprises one of doxycycline and methotrexate. Moreover, such strips preferably include between 0.2 and 0.9% xylitol by weight. Also, such strips may further include an effective amount of paquinimod such that when applied to a tooth area of the subject, is effective to inhibit collagenase activity. In still other embodiments the strip comprises one of bioluminescent material, compounds that facilitate the growth of desired bacteria beneficial to a person's health, and/or at least about 200 mg. xylitol. One will appreciate that the strips can have various constructions and structures to facilitate functional aspects sought to be achieved. For example, certain embodiments employ strips having encapsulated materials that can elute from the strip at particular times or via the purposeful rupture of an encapsulated (e.g. frangible by pressure) structure so as to cause the release of an encapsulated material or composition. In some embodiments, a strip having encapsulated pockets may include one of *Prevotella*, iron, NO, antibiotics, anti-biofilm agents and/or anti-inflammatory agents, etc. thus rendering it possible to apply a customized strip to a person's oral cavity to effectively address the particular situation.

Porphyrmonas gingivalis is one of the major etiological agents involved in advanced adult periodontitis and its virulence factors, such as lipopolysaccharide, fimbriae, haemaglutinins, vesicles and proteases, have been characterized. Among these virulence factors, arginine-specific cysteine proteinase (Arg-gingipain, Rgp) and lysine-specific cysteine proteinase (Lys-gingipain, Kgp), which specifically cleave synthetic and natural substrates at the carboxyl sides of arginine and lysine residues, respectively, have received considerable attention due to their strong ability to degrade a broad range of host proteins. Rgp and Kgp activities cause not only destruction of periodontal tissue but also disruption of host-defense mechanisms. Rgp is involved in fimbriation.

The initial step of *Por. gingivalis* attachment to the oral tissue has been shown to be fimbriae-mediated and the attachment can be achieved by *Por. gingivalis* adherence to micro-organisms that have already colonized the periodontal regions. *Por. gingivalis* can co-aggregate with *Prevotella intermedia*, which is one of the early colonizers in periodontal niches. Co-aggregation among bacterial cells caused by the adherence of one bacterial species to another is a colonization mechanism. There are several aggregation factors for co-aggregation between *Porphyromonas* (Por.) *gingivalis* and *Prevotella* (Pre.) *intermedia*. Moreover, as part of the infective process, *Porphyromonas gingivalis* must acquire heme which is indispensable for life and enables the microorganism to survive and multiply at the infection site. A hmu heme uptake system with a leading role played by the HmuY hemophore-like protein, is responsible for acquiring heme and increasing virulence of this periodontopathogen. *Prevotella intermedia* produces two HmuY homologs, termed PinO and PinA.

Several virulence factors contribute to differences in the bacterial virulence of *P. gingivalis*, in particular the *Fimbriae* and hemagglutinins. Based on the diversity of the fimA gene, fimbriae are classified into six genotypes (I-V and Ib) (Hamada et al., 1994; Nakagawa et al., 2000), being type II fimbriae, followed by type IV, the most frequently found in *P. gingivalis* strains isolated from periodontitis patients (Amano et al., 2000, 2004; Missailidis et al., 2004). In contrast, healthy adults carry strains coding type I fimA (Amano et al., 2000). *P. gingivalis* possesses at least eight hemagglutinins encoded by the hag genes (hagA to hagE) (Progulske-Fox et al., 1989, 1995; Nelson et al., 2003). Among them, the hemagglutinins HagA, HagB, and HagC have been described as important virulence factors (Belanger et al., 2012; Connolly et al., 2017). A number of virulence factors have been reported to contribute to the pathogenicity of *P. gingivalis* including; LPS, fimbriae, hemagglutinin, hemolysin and extracellular hydrolytic enzymes (especially the Arg-X and Lys-X specific proteinases), otherwise known as "*P. gingivalis* trypsin-like enzymes".

Porphyrmonas gingivalis, a keystone pathogen of periodontal disease, has been reported to be associated with human Alzheimer's Disease (AD). The inflammatory burden following oral infection and entry of this bacterium into the brain appears to drive the formation of amyloid-beta plaques and neurofibrillary tangles with loss of cognition. *P. gingivalis* is a master of immune subversion in this inflammatory cascade and may establish microbial dysbiosis where it is located.

Gingipains are involved in AD in that they are believed to enhance the effect of polymorphic complement gene defects, allowing for a local infection and the recruitment of additional bacteria that are resistant to the bactericidal activity of complement.

An ideal window to control the impact of peripheral inflammation from periodontitis on AD is at the time of diagnosis of the or disease. The clinical value of inhibiting all the three main pathways of complement activation was recently suggested in periodontitis and can be achieved by targeting the central component C3, which directly inhibits inflammation and indirectly counteracts dysbiosis. Gingipain inhibitors (Kgp) are valuable for treating *P. gingivalis* colonization of the AD brain.

To further comply with written description and enablement requirements, the following are incorporated herein by reference: 20190315642 to Parsley; 20170246269 to Hajishengallis; 20130236488 to Dashper; and 20030083287 to Burgess.

Orally administering to the subject after at least 24 hours after removal of said strip from the subject a pharmaceutically effective amount of a preparation comprising *Prevotella intermedia* bacteria that produces nitric oxide is believed to be effective in that such an oral bacterial population mimics that observed in the Amish populations where the incidence of AD is rare. Yet further methods involve the provision of a strip to a person who has been diagnosed with periodontitis and includes use of a strip that includes an effective amount of *Prevotella intermedia* that has been modified to remove at least one virulence factor, as well as at least about 200 mg. xylitol and an effective amount of paquinimod to inhibit collagenase activity.

These and other aspects of the present invention are described herein, offering for the first time, both a causative explanation for AD, as well as practicable and beneficial ways to reduce its progression.

BRIEF DESCRIPTION OF THE DRAWINGS

FIG. 2A-2D illustrate various illustrations of oral strips that have micro surfaces that deter bacteria from residing on such surfaces.

DETAILED DESCRIPTION OF PREFERRED EMBODIMENTS OF THE PRESENT INVENTION

Figure 1:
FIG. 1 shows a photograph of Dr. Alios Alzheimer for which the disease sought to be treated via the present invention is named after.

FIG. 1 shows a photograph of Dr. Alios Alzheimer for which the disease sought to be treated via the present invention is named after. It is interesting that the prevalence of AD is so recent. Discovered in 1906 as a rarity, AD has now become one of the top health concerns in the world. The rise in AD raises questions as to what present practices are causing its progression. As described herein, while preventative dental health is one way in which to combat AD, the present inventors also believe that the rise of dentistry during the last 100 years has also played a causative role in AD in that it is much more common today for a person to engage in activities where their gums bleed, thus providing a route for various oral microbes to enter the blood stream and cause various diseases, including AD, arteriosclerosis, some types of inflammatory arthritis, etc.

According to various aspects of the present invention, one critical appreciation relates to the inventors' contention that bacterial infections are at the heart of many of today's chronic diseases. For example, it is believed that periodontal disease is a risk factor for cardiovascular disease and stroke, as well as a host of other diseases mentioned herein, including Alzheimer's disease, IBD, Crohn's Disease, etc. Because periodontal disease is a modifiable risk factor that can be prevented and treated—the long felt but unsolved treatments for various chronic diseases can also be prevented and treated. Thus, employing a combination of a restorative microbiome approach and an antimicrobial approach, provides for the implementation of treatment that is specifically designed to improve a person's periodontal condition so as to reduce and/or delay future chronic disease, with Alzheimer's disease being one of many. It is believed that one of the reasons such an approach has not earlier been adopted is that when it comes to dental health, there exists several centuries of dental teaching that states that periodontal disease results from a "dirty mouth." Thus, suggesting the use of microbes in the oral cavity to alleviate disease may appear to many as being counterintuitive and as a "teaching away" from long held beliefs and practices.

Periodontal diseases are very common, affecting up to 90% of the global population. The common inflammatory forms of the diseases are caused by pathogenic microflora in the biofilm or dental plaque that forms adjacent to the teeth on a daily basis and can result in loosening of teeth, occasional pain, and eventual tooth loss. Several Gram-negative bacteria, including Porphyrmonas gingivalis, *Treponema denticola*, and *Tannerella forsythia*, are frequently isolated from dental plaques in periodontal patients and were initially considered periodontal pathogens. A strong correlation between several cultivable bacteria such as *Prevotella intermedia, Fusobacterium nucleatum, Aggregatibacter actinomycetemcomitans*, and *Eubacterium nodatum* and periodontal disease has also been reported. Although subgingival bacteria are the major cause of periodontal diseases, more than one-half of subgingival bacterial species or phylotypes are not readily cultivable, which presents an obstacle to fully understand the causal relationships between subgingival bacteria and periodontitis. To overcome the difficulties and limitations associated with cultivation, culture-independent methods based on amplification and sequencing of bacterial metagenomes have been developed to identify thousands of different bacteria in a single sample.

There are two main forms of periodontal disease: gingivitis and periodontitis. Both are pathologic periodontal inflammatory processes that are the result of an accumulation of dental plaque. The most common is the plaque-induced gingival disease called gingivitis, which is a reversible form of periodontal disease. The other form of periodontal disease is periodontitis, a destructive, irreversible, chronic inflammatory process due to dental plaque, which results in atrophy or loss of the underlying bone and connective tissue support around the teeth. Periodontitis is the most common chronic inflammatory disease known to mankind.

The present inventors believe that effective management of periodontitis is a key to the prevention of Alzheimer's disease, as periodontitis is both treatable and preventable. Thus, oral health is directly related to brain health and with purposeful reduction in the numbers of certain bacteria and exposure to certain bacteria species, such as in certain embodiments, *Prevotella*, the benefits of decreased periodontitis, and thus, the reduction in the emergence of Alzheimer's disease, can be achieved. Prevention of Alzheimer's disease through the use of microbiome products is believed to be one of the best ways to avoid the prevalence of Alzheimer's disease and the public expenses related to its management.

Periodontitis is a common oral infection associated with primarily gram negative anaerobic bacteria. Periodontitis is an inflammatory disease caused by a microbial biofilm, characterized by periodontal pocket formation, attachment loss and loss of supporting alveolar bone. Periodontally compromised teeth lose function and may have to be extracted, which often requires costly prosthetic rehabilitations. In industrialized countries, approximately 50% of the adult population suffers from moderate or severe periodontitis.

Dental plaque is unlike any other bacterial ecosystem. Plaque is divided into two distinct types based on the relationship of the plaque to the gingival margin, i.e., supragingival plaque and subgingival plaque. The subgingival plaque harbors an anaerobic gram-negative flora has been associated with Periodontitis. Periodontitis can be marked as a "low-grade systemic disease" by release of proinflammatory cytokines into systemic circulation and elevation of C-reactive protein (CRP).

Although bacteria are involved in periodontal infections, it is not the scenario of a typical infection, as the offending bacteria generally remain outside the body, attached to the tooth. When gum disease reaches a bleeding stage, the bacterial components of the plaque changes and there is an increase in various species, including *Prevotella* species, which have nutritional requirements derived from the host, such nutrients becoming available as a result of the tissue inflammation and bleeding.

While not bound by theory, *Prevotella* in an individual's oral cavity, due to its production of nitric oxide, plays a beneficial role in maintaining oral health in a fashion that prevents AD progression. While *Prevotella* is also seen in biofilms that may ultimately also be involved in providing conditions for spirochetes to be protected and grow, and ultimately to be released into the blood or along nerves to reach the brain, the presence of *Prevotella* should not automatically be considered as a negative. The conventional thinking that various of the bacteria found in one's oral microbiome are clearly categorized as either "good" or "bad" is outdated and largely inaccurate. Depending upon other conditions, the presence of particular bacteria previously deemed to be pathogenic, may indeed serve a beneficial role in maintaining a person's oral microbiome health, including in establishing a better oral microbiome to prevent the progression of AD.

While there are over 500 species of microbial species that are believed to be primary etiologic agents for periodontal disease, only a relatively small number most frequently associated with active periodontal disease, including gram negative, anaerobic pathogens: Porphyrmonas gingivalis, *Tannerella denticola, Tannerella forsythia; Fusobacterium nucleatum, Prevotella intermedia, Prevotella nigrescens, Peptostreptococcus micros, Campylobacter rectus, Centruroides gracilis, Campylobacter showae, Eubacterium nodatum*, and *Streptococcus constellatus*. Thus, only a limited number of gram-negative anaerobes are significantly associated with periodontal disease. Various embodiments of the present invention are focused on the more refined selection of an appropriate drug to employ to combat particular gram negative, anaerobic pathogens.

Current treatment for periodontitis involves removal of all bacteria from the subgingival pockets. Removal of subgingival plaque by current treatment methods is temporary, since the subgingival packet may be re-colonized after cleaning by organisms from the supragingival reservoir. For individuals suffering periodontal disease, current practice also involves the use of antimicrobial agents that are typically chosen to kill as many bacterial types as possible, often employing broad-spectrum agents such as tetracycline, amoxicillin and metronidazole, and often leading to the overuse of these agents. While use of antimicrobial agents plays a part in various embodiments of the present invention, such use is more nuanced and the destruction of beneficial bacteria in the oral cavity is either prevented or reestablishment of such bacteria is fostered so as to maintain a healthy oral microbiome that can prevent periodontal disease, and thus also prevent the onset of Alzheimer's disease. The uncritical use of antibiotics could increase bacterial resistances. One goal of the present invention is to preserve the maintenance of an ecologically balanced biodiversity of the microflora within the oral cavity as it is crucial not only to the oral health but also to the general health of the individual, especially in avoiding Alzheimer's disease.

Surprisingly, clinicians have been advised that they do not really have to test for what microbe might be involved in periodontitis, and instead may simply use antibiotics on an empirical basis to see how they might work. Thus, one aspect of the present invention is to halt such indiscriminate use of antibiotics—and to have the clinician carefully evaluate the presence of specific gram positive anaerobic bacteria that cause periodontitis, and more importantly, to re-administer beneficial bacteria to the oral cavity after antibiotic treatments. Indeed, current practice for the treatment of chronic periodontitis includes a recommendation to use more than one antibiotic with different antibacterial spectra under the misguided belief that a broad diversity of periopathogens must be killed, including anaerobic, microaerophilic, and aerobic bacteria, both Gram negative and Gram positive. One aspect of the present invention is to target particular gram negative organisms, specifically not including other organisms, such as *A. Actinomycetemcomitans*, as the use of antibiotics against this organism is believed to hinder, rather than promote, the objective of establishing a healthy microbiome that prevents Alzheimer's disease.

The progress in finding treatments for periodontal disease has been hindered in that there has been no consensus as to whether an anaerobic or microaerophilic infection is involved. Only recently have studies shown that *A. actinomycetemcomitans* is not, as was previously assumed, an important periodontopathogen in major periodontal diseases. Its reintroduction after antibiotic treatment is therefore one aspect of several embodiments of the present invention.

A broad based antibiotic therapy as part of an early treatment regimen in patients diagnosed with Alzheimer's disease, without an appreciation of the wider beneficial aspects of the oral microbiome—could lead to a worsening of Alzheimer's disease, rather than a treatment for it. As described herein, a similar concern relates to destruction of biofilms without an appreciation of how spirochetes may thus be freed to inflict further damage. Indeed, in various embodiments of the present invention, there is a fostering of the establishment of certain oral bacteria populations, e.g. *Prevotella* bacteria, etc. which would be killed by indiscriminate use of antibiotics.

Treatment for patients in the early stages of dementia may require more that the administration of antibiotics, such as penicillin, as penetration through oral biofilms necessitates the use of an effective agent to disperse the biofilm. Such anti-biofilm agents include, for example, furans (citalopram), thiophenes (olanzapine), piperidines (donepezil), pyrroles (azoles), [and rifampin. Donepazil (an anticholinesterase inhibitor and also a biofilm disperser) is a preferred anti-biofilm agent for incorporation into the oral strips of the present invention such that it can elute directly onto gum an tissue, thus avoiding the need for systemic administration of drugs that would have deleterious effects on other parts of the body not being treated for biofilm formation.

Importantly, while biofilm formation in the oral cavity is sought to be disrupted so as to enable the killing of undesired bacteria, the dispersal of biofilm formation in a person's brain must be considered with special caution. This is so because dispersal of a biofilm and the release of spirochetes bacteria form such biofilm, may result in the unintended spread of the spirochetes to other regions where similar biofilm and plaque buildup may occur. The dispersal effect in such cases would therefore potentially create many more plaques, e.g. the use of haloperidol in treating AD has been shunned. Thus, in certain embodiments, and especially for early dementia, penicillin is preferably administered, in some situations both systemically and in the more concentrated strip contacting form, In treatment of the "latent" stage of AD, the use of penicillin or other suitable antibiotics is advisable, but with the caveat that disruption of the biofilm and plaque structures should be carefully considered so as not to spread spirochetes throughout the body and brain tissue. Dosages, etc. for antibiotics would be similar to those employed in the treatment of latent syphilis. Moreover, treatment of a person with appropriate antibiotics prior to any dental surgery is recommended to avoid unintended release of spirochetes into a person's bloodstream. This entails treating the spirochetes before they reach the brain in the case of dental surgery and before they do damage or get caught in biofilms or plaques in latent disease.

Combinations of antibiotics may be employed to enhance the effect of individual antimicrobials through synergic interactions and for the treatment of biofilm-associated infections. For example, rifampin, vancomycin and fusidic acid may be used in combination with other listed antibiotics to achieve the control of spirochetes infections, especially via the incorporation of these agents in the strips as described herein as an effective way to disperse biofilms and render antibiotics more effective against spirochetes and associated bacteria in combating various biofilm-associated diseases. Various antibiotics can be employed with the strip embodiments of the present invention, including but not limited to: daptomycin, daunomycin, doxorubicin, and mitomycin C that had good activity against B. burgdorferi; and plant-made antimicrobial peptides such as retrocyclin and protegrin.

In various aspects of the present invention, the disruption of biofilms is achieved via one or more agents that are preferably incorporated into a strip for use in the oral cavity of a person. By even partially disrupting the biofilm structure, the remaining in the oral cavity and especially those bacteria contributing to a biofilm, can become more vulnerable to antimicrobial agents. Therefore, substances that affect biofilm biomass are believed to be of considerable utility for the treatment of biofilms in that disruption thereof can assist in treating spirochetes infection in the oral cavity before spirochetes are able to travel to a person's brain tissue. In certain preferred embodiments, one of xylitol and farnesol are employed to facilitate degradation of a biofilm in the oral cavity. In still other embodiments, sodium hypochlorite is used as an anti-biofilm agent, preferably in at least about a 6% concentration. In addition, there are many commonly prescribed medications that have additional abilities to act as systemic biofilm dispersers. These include piperidines: (donepezil, haloperidol, risperidone), thiophenes (olanzapine), furans (citalopram), and pyrroles (leflunomide, itraconazole, celecoxib, and atorvastatin).

In various embodiments, one aspect of the present invention is directed to therapies to treat or prevent the onset of periodontal disease, which in some embodiments that target agents that inhibit the adherence of *P. gingivalis* to supragingival plaque, such as can be included in mouth rinses and toothpaste formulations, so that they may be easily and non-invasively administered. *P. gingivalis* gains systemic exposure through damage to gingival tissues. Therefore, while not bound by theory, one aspect of the present invention relates to limiting *P. gingivalis* adherence to supragingival plaque in the oral cavity has a dramatic effect on systemic diseases, including atherosclerosis and Alzheimer's disease.

In preferred embodiments, the prevention of the growth of particular pathogenic organisms is achieved without destruction of other helpful organisms that inhabit the oral cavity. In certain embodiments, agents are employed to prevent particular biofilms, such as *P. gingivalis* biofilms, to establish an oral microbiome environment that will halt the progression of Alzheimer's disease. Incorporated herein by this reference in their entireties are the following US patents and patent publication nos.: 20120142548 to Corsi et al.; U.S. Pat. Nos. 6,287,610, 6,569,474, US20020009520, US20030206995, US20070054008; and U.S. Pat. No. 8,349,313 to Smith; and U.S. Pat. No. 9,011,834 to McKenzie.

FIG. 2A-2D illustrate various illustrations of oral strips that have micro surfaces that deter bacteria from residing on such surfaces. In particular embodiments of the present invention, an oral strip, preferably mucoadhesive in nature and preferably with xylitol therein, is employed to apply a locally acting collagenase inhibitor agent. Xylitol, for example, included with such strips, reduces bacteria growth. Other oral strip embodiments include the provision of active agents in addition to (or not) the antibacterial surface structures as described herein as illustrated in FIGS. 2A-2D. After applying such strip to the oral cavity, it is able to release a preferred agent or drug slowly as it is dissolved, so that the drug concentration in saliva exists for an extended time and maintains the desired inhibitory concentration. Blood and saliva are similar in many respects, but due to blood being conveyed outside the oral cavity, it poses a significant route for bacteria to infect various other portions of one's body. Treating oral bacteria while in the oral cavity is therefore a preferred way to address bacterial populations so as to control their detrimental effects if and when they escape the oral cavity. Altering the conditions in a person's oral cavity so that a preferred population of oral bacteria are fostered is one aspect of the present invention. The oral strips as described herein may include various agents, such as xylitol, antibiotics, beneficial bacteria, etc. that provides for the ongoing and low dose concentrations required for certain bacteria to thrive and others to not thrive. Moreover, inclusion of encapsulated pockets in such oral strips provides a way to introduce preferred bacteria into the oral cavity. Thus, providing modified *Prevotella* bacteria (e.g. modified so as to reduce or hinder various virulence facts of a native *Prevotella*) is one way in which to encourage the growth of bacteria in a person's oral cavity in a manner that is believed to be beneficial in deterring the progression of AD.

Such antibacterial structures as illustrated in FIG. 2A_D interfere with the formation of biofilms that would otherwise form in a person's oral cavity. By disrupting biofilm formation, one is able to hinder the progress of biofilms that are associated with the progression of periodontitis and in such a way, interfere with the progression of AD. The coating of dental surfaces—as well as the mucous membranes inside the oral cavity—sing the anti-bacterial surfaces as described herein, and in particular those as described in one of the parent applications to the present case, may be employed to further reduce the number and type of undesired bacteria in the oral cavity.

Use of the strips of the present invention also overcomes certain problems with conventional formulations of doxycycline hydrochloride, including undesired gastrointestinal reactions that produce systemic toxicity, and further eliminates complications arising from the use of drug infused chips, which are inserted into periodontal pockets as well as other resorbable gel compositions, which provide for controlled-release of doxycycline for approximately one week. As Periostat® requires twice daily dosing and raises concerns about patient compliance, the strips of the present invention are believed to be superior and highly beneficial in terms of compliance and effectiveness, without overdosing of drugs in a manner that may cause problems stemming from the long-term administration of antibiotics and consequential reduction or elimination of healthy biotic flora, such as intestinal flora, which can lead to the production of antibiotic resistance organisms or the overgrowth of yeast and fungi. Thus, the strips of the present invention provide a unique way to achieve the benefit of anti-collagen destructive enzymes while avoiding other undesired antibacterial effects.

Figure 3:
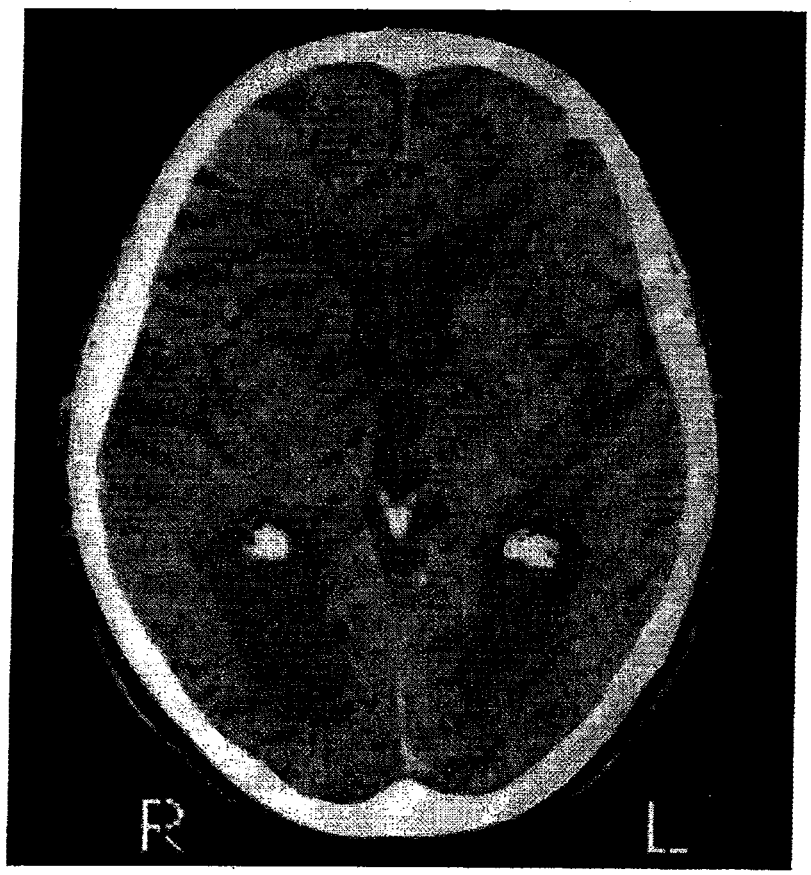
FIG. 3 illustrates a CAT scan section of a human brain showing evidence of Alzheimer's disease.

Alzheimer's disease was thought to be a disorder related to synthesis and decline in the degradation of AβP. FIG. 3 illustrates a CAT scan section of a human brain showing evidence of Alzheimer's disease. There is recent and compelling evidence that Aβ, however, is not simply a misfolded protein that accumulates in the brain, but is instead a protein with physiological roles that responds to several pathological contexts. The pathological process of Alzheimer's disease is thought to begin long before the diagnosis of dementia is made and thus, an appropriate targeted treatment should start early in order to prevent dementia.

Periodontal disease is an inflammatory disease in which the inflammatory response, followed by the acquired immune response, drives the pathogenesis of periodontal tissue destruction. Periodontal pathogens, which are more or less universally present in low numbers, use inflammation to provide an environment to foster their growth. While for a long time it was thought that bacteria was the factor that linked periodontal disease to other diseases in the body, more recent research demonstrates that inflammation may be responsible for the association. One aspect of the present invention is directed to the appreciation that preventing and treating inflammation involved in periodontitis (and the resultant increase in host-derived, tissue-destructive enzymes, e.g., collagenase plus other matrix metalloproteinases (MMPs), will help with the management of other chronic inflammatory conditions, including Alzheimer's disease.

The foundational characteristics of all inflammatory diseases is the up-regulation of cytokines, prostaglandins, MMPs (i.e. host derived, tissue-destructive matrix metalloproteinases), reactive oxygen species, etc. A major event in the link between local periodontitis and relevant systemic/medical conditions is the release, from the inflamed periodontal tissues of inflammatory mediators into the bloodstream, which subsequently travel to the liver. Once inflammatory mediators are present in the blood (i.e. derived from the inflamed gingiva), the liver is stimulated to produce acute phase proteins, which are diagnostic markers and mediators of inflammatory disease; one being C-reactive protein (CRP). To add insult to injury, LDL (low density lipoprotein) cholesterol, when oxidized by the inflammatory response, then forms a chemical reaction with CRP. The end result is a complex of oxidized LDL combined with CRP, which is taken up by macrophages in the atheroma and these macrophages differentiate into foam cells, found in lipid-laden plaques in the arteries and that are associated with increased risk of heart attack and stroke. The foam cells, in turn, release MMP's, such as MMP-8, also known as collagenase. Collagenase's primary function is to break-down collagen. A collagen rich protective cap that encapsulates atherosclerotic plaque is thus destroyed by collagenase, often leading to a thrombosis, followed by stroke or a heart attack. Thus, while a principal focus of the present invention is on the prevention of Alzheimer's disease, one of skill in the art will appreciate the various other important diseases may also be addressed via the guidance provided in the present specification, and such other aspects should be understood as also being a part of the present invention.

While the human body is continually destroying old collagen, followed by a renewal process of normal turnover, in chronic inflammatory disease, collagenases, particularly MMP-8, become excessive and the normal repair process is halted. The inflammatory mediators (cytokines, prostaglandin, MMPs) present with oral inflammation, flow into the blood bi-directionally from the gingiva into the circulation, resulting in systemic inflammation. Thus, unless there is a cessation of the inflammatory response, treatment is rendered difficult, if not impossible.

Slowing down the breakdown of collagen and/or inhibiting the production of collagenase is thus one aspect of the present invention and is one way in which to prevent the progression of Alzheimer's disease. Collagen degradation can be inhibited, for example by using TIMP proteins (tissue inhibitors of metalloproteinases). To reduce potential degradation of polypeptides, certain tripeptides may be employed as collagenase inhibitors, as well as other collagenase inhibitors, e.g. such as paquinimod, and those one of skill in the art will appreciate can be employed for the present purposes, see e.g., U.S. Pat. Nos. 4,687,841 and 4,720,486 to Spilburg, et al.; US patent publication no. 20070207955 to Tanihara; all incorporated herein by this references).

It is known that tetracyclines, a class of drugs that had previously been recognized only as antibiotics, were unexpectedly found to block collagenase in mammals. This lead to the development of a formulation of doxycycline that inhibits collagenase (MMP-8) and other MMPs at a blood level so low that it would NOT perform as an antibiotic known under the trade name, of Periostat®. Low dose or subantimicrobial dose doxycycline is the first systemically administered collagenase inhibitor drug approved by the U.S. FDA. In particular embodiments of the present invention, a topical and locally acting collagenase inhibitor agent, similar to doxycycline, is employed to treat periodontitis, which will act to prevent the progression of Alzheimer's disease. In one embodiment, an individual at risk of further developing periodontitis is administered doxycycline plus methotrexate (MTX), preferably a low dose (about 20 mg) of doxycycline twice daily with MTX.

One aspect of the present invention is to provide antimicrobial agents formulated into oral care products to augment mechanical plaque control. A delicate balance is needed, however, to control the oral microbiota at levels compatible with health, without killing beneficial bacteria and losing the key benefits delivered by these resident microbes. In certain embodiments, the strips as described herein are employed or this purpose. Importantly, in various embodiments of the invention, instead of focusing on the destruction of one particular species of bacteria, the native bacterial populations of an individual are adapted to remove particular virulence factors from such a species. The destruction of the native oral bacteria and the replacement of such bacteria with the above described modified bacteria, e.g. having impaired virulence facts, is one way in which to reduce the formation of undesired biofilms that can harbor spirochetes that are the root cause of AD. One of skill in the art, especially with the employment of CRISPR-Cas systems, is therefore able to adapt native bacteria form a person's oral microbiome and transform such a population to enhance the overall health of the oral cavity and in a manner that reduces the chances that AD will progress.

To comply with written description and enablement requirements, incorporated herein by the following references are the following patent publications: U.S. Patent publication Nos. 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 2015/0132263 to Liu; and 2014/0068797 to Doudna; U.S. Pat. No. 8,945,839 to Zhang; 2014/0255351 to Berstad et al.; 2015/0086581 to Li; PCT/US2014/036849 and WO 2013026000 to Bryan; 2016/0199424 to Berry et al.; 2013/0326645 to Cost et al.; 2016/0206666 to Falb; 2017/0042860 to Kashyap and 2015/0045546 to Siksnys; U.S. Pat. No. 10,730,826 and 2020-0148642 to Konradi, et. al.; 20210321756 to McLaughlin, et. al; 20160199424 to Berry, et. al.; 20210308028 to Yang, et. al.; and U.S. Pat. No. 11,083,760 to Han; 20180110795 to Frias-Lopez; and 20210169954 to Balani et. al.

One aspect of the present invention is directed to the maintenance of a population of *Prevotella* bacteria in the oral cavity that is similar to populations found in healthy Amish individuals where Alzheimer's disease is a rarity. Amish individuals were found to have elevated levels of *Prevotella* in their oral cavity as compared with other individuals. *Prevotella* is known to produce nitric oxide. Nitric oxide (NO) is known to have potent antimicrobial properties and is an important cellular signaling molecule. NO is a free radical with an unpaired electron. Although the earliest studies in the field suggested that NO is a strictly pro-inflammatory macrophage product, it is clear from the current literature that, in fact, NO is made by numerous cell types and is often anti-inflammatory. Much of this dichotomy can be explained by the particular responses of given cells involved in the inflammatory response, but another variable involves the complex chemistry in which NO can participate.

Nitric oxide is a ubiquitous intercellular messenger molecule with important cardiovascular, neurological, and immune functions. Nitric oxide is a short-lived, reactive free radical that participates in a variety of reactions and in small controlled concentrations in the body, it acts as a physiological and pathophysiological mediator and it plays an important role in biological systems. The assessment of the stable end products of NO, nitrite and nitrate (NOx), is commonly used as a measure of the NO production in biological fluids. The production of nitric oxide represents a mechanism of pathogen destruction in activated neutrophils. Production of NO or expression of inducible NO synthase (iNOS) by peripheral neutrophils or in gingival tissues is associated with periodontal disease. The massive presence of neutrophils and their enhanced activity at sites of periodontal disease have sparked debate as to whether neutrophils are responsible for the destruction of periodontal tissues or whether they play protective roles in controlling pathogenic bacteria involved in periodontal disease. Neutrophils from periodontitis patients produced significantly lower levels of NO levels when compared to neutrophils from healthy subjects. Low NO levels were produced by neutrophils from chronic periodontitis patients. So the presence of NO seems to be desired in avoiding periodontitis. *Prevotella* is associated with increased NO production and thus, *Prevotella*—while also associated with periodontitis, is oddly believed to be beneficial to individuals. The recruitment of neutrophils and other leukocytes in the periodontal pocket is an important feature of the inflammatory process in periodontal disease. Neutrophils play an important role in periodontitis by producing nitric oxide (NO) and antimicrobial peptides, molecules with microbicidal activity via oxygen-dependent and -independent mechanisms, respectively. The use of nitric oxide to disperse biofilms may be employed to improve infectious disease treatments. The use of low levels of NO to exploit its signaling properties to induce dispersal represents an unprecedented and promising strategy for the control of biofilms in clinical contexts.

*Prevotella*, previously classified in the genus *Bacteroides*, is a genus of an obligate anaerobic gram-negative rod-shape bacterium. Although they generally have a limited ability to ferment amino acid and require hemin and menadione to grow, *Prevotella* is a versatile genus which has been observed in various niches, such as oral cavity, upper respiratory tract, urogenital tract, rumen and human feces. *Prevotella* is also well-known as a preventative agent for the bovine disease of rumen acidosis. Rumen acidosis greatly affects milk production of cattle by disrupting the typical digestive processes of the stomach. As another indication that *Prevotella* may be beneficial, this leads to an increased susceptibility to other pathogenic forces which also affect the health of food provided from the cattle.

Periodontal diseases are chronic inflammatory infections associated with gram-negative bacteria which stimulate macrophages to generate NO. *Prevotella intermedia* has conventionally been considered to be one of the causative pathogens of periodontal disease. The increased population of such bacteria in healthy Amish individuals, however, coupled with the scarcity of Alzheimer's disease in the Amish population, presents a classic case where one of ordinary skill in the art of periodontitis treatment, would not promote the use of *Prevotella*.

Chronic inflammation is characterized by a proliferation of fibroblasts and formation of blood vessels (angiogenesis), as well as an influx of chronic inflammatory cells, namely granulocytes (neutrophils, eosinophils, and basophils), lymphocytes, plasma cells and macrophages. Nearly two decades ago, the production of nitrogen oxides was associated with inflammation. The metabolic pathway known as the Larginine: NO pathway is the main source for the production of NO in mammalian cells by a group of enzymes known as the nitric oxide synthases (NOS). The enzyme primarily responsible for the roles of NO in inflammatory processes is the inducible NOS (iNOS; NOS2; or type II NOS), which is not typically expressed in resting cells and must first be induced by certain cytokines or microbial products.

In recent years, NO has emerged as a major mediator of inflammation. As might be expected from such a pleiotropic molecule, there are contradictory reports in the literature concerning its role as an anti-inflammatory or proinflammatory agent. The inconsistencies reported probably are due to the multiple cellular actions of this molecule, the level and site of NO production, and the redox milieu into which it is released.

The dichotomous role of NO in inflammation, often referred to as the NO paradox, is based mainly on the conflicting data showing the effects of NOS inhibitors of varying selectivity in different animal models. The physiological and pathological functions of NO are diverse and often contradictory. NO acts as a useful endogenous free-radical scavenger. NO may provide a chemical barrier to cytotoxic free radicals. NO may have a considerable protective effect on cellular viability and can act as an antioxidant protecting cells from oxidant-induced damage and preventing endothelial apoptosis. Low NO concentrations contribute to endothelial cell survival and high NO levels induce the apoptosis of endothelial cell. Any assessment of the role of NO in human disease must take into account the dual role of NO.

Many of the regulatory and physiological functions of NO can be considered as protective or "anti-inflammatory," and are mainly related to NO produced by the other isoforms of NOS. Other data exists, however, that iNOS expression is found in an increasing number of human disorders, for example, nitric oxide is crucial in the pathogenesis of septic shock. It is believed that certain microorganisms have developed means for suppressing the expression and/or activity of iNOS, perhaps by co-opting the host's own regulatory machinery. Viewed from this perspective, the balance between induction and suppression of iNOS may underlie much of the physiology and pathology of inflammation. Nonspecific inhibition of iNOS also has been reported to be detrimental, rather than beneficial. Release of NO has been reported in inflammatory responses initiated by microbial products or autoimmune reactions. The effects of NO on specific immunity is under investigation. Most of the existing data suggest that NO suppresses, rather than enhances, lymphocyte activation and proliferation. One possible explanation for these often contradictory results is that iNOS inhibition is detrimental to the host during priming of pathogenic T-cell responses in the periphery, but largely protective at the site of disease. It appears that NO plays an important role in the pathogenesis of chronic inflammation. Nitric oxide stimulates TNF-_production by synoviocytes and its catabolic effects on chondrocyte function promote the degradation of articular cartilage implicated in certain rheumatic diseases. Studies indicate that NO is at least partly responsible for IL-1-induced suppression of glycosaminoglycan and collagen synthesis. In human chondrocytes, IL-18 has been identified as a cytokine that regulates chondrocyte responses and contributes to cartilage destruction through stimulation of the expression of several genes, including iNOS, inducible COX, IL-6, and stromelysin. Although most experimental findings suggest that the actions of NO in the cartilage are detrimental, there is also evidence for protective functions of NO. In a recent study, intravenous inoculation with *S. aureus* induced significantly increased clinical severity of septic arthritis, with attendant septicemia in iNOS deficient mice, compared with similarly infected heterozygous or wild-type mice. This was associated with enhanced production of IFN-_ and TNF-_ in vivo and in vitro, which indicated a shift towards increased production of Th1-type cytokines. Apart from antimicrobial activity, other beneficial effects of NO include stimulation of proteoglycan synthesis during certain conditions, participation in wound healing, and stimulation of collagen production. Furthermore, NO also is reported to promote mucosal integrity. The isoform nonselective NOS inhibitor L-NAME worsens acute edematous and necrotizing pancreatitis; whereas, NO donors reduces pancreatic injury. Indeed, there is increasing evidence that iNOS is beneficial, rather than detrimental, for resolving intestinal inflammation. Evidence for the dual roles of inducible NO in modulating gastrointestinal mucosal defense and injury. Periodontal diseases and inflammatory bowel disease, both chronic inflammatory diseases, are believed to be related, as induction of periodontal disease results in gut dysbiosis. In endothelial cells, NOS prevents apoptosis; whereas, it induces apoptosis in smooth muscle cells. The presence of iNOS in atherosclerotic plaques suggests a role for NO in atherosclerosis but its exact role is still unknown. One of the primary functions of the inflammatory response is to heal wounded tissue. Healing commences soon after injury, while acute inflammation in still in full swing. Interestingly, the cytokine most associated with wound healing, TGF-_1, may be the most potent suppressor of iNOS. One of the roles of iNOS in wound healing may be to modulate TGF-_1. Caution with the use of iNOS inhibitors is warranted in settings that require appropriate wound healing.

It is now clear that NO cannot be rigidly catalogued as either an anti-inflammatory or a proinflammatory molecule, but it can be considered a true inflammatory mediator. Inducible, high-level NO production mediates a number of inflammatory and infectious diseases by acting both as a direct effector and as a regulator of other effector pathways. Thus, while in a preferred embodiment, the production by

*Prevotella* present in a person's mouth is adjusted to mimic the levels observed in healthy Amish individuals, in certain embodiments, e.g. where other factors indicate that excessive, and thus detrimental levels of NO are being produced, one aspect of the present invention is to address the cytotoxic and damaging actions of NO/RNOS without interfering with essential protective functions. Besides selectively inhibiting iNOS, a number of other therapeutic strategies are conceivable in order to alleviate the deleterious effects of excessive NO formation. These alternative therapies involve scavenging of NO/RNOS, and/or inhibition of metabolic pathways triggered by these molecules. The advantage of preserving the beneficial effects of iNOS also needs to be considered when implementing any therapeutic approach. The identification of the roles of NO and of the cells that produce it, as well as the more complete elucidation of the mechanisms that regulate its cellular production in inflammation, will help in the development of therapeutic applications for both acute and chronic inflammatory diseases. Mitochondria preserved some key features of prokaryote synthesis, demonstrating the evolutionary basis to the NO synthesizing prokaryote world.

In particular embodiments, a mucosal, e.g. oral, strip is provided with an effective amount of an agent effective to non-systemically reduce numbers of undesired bacteria in an individual's oral cavity. In one embodiment, the agent comprises Azithromycin, which has been found to be effective against anaerobes and gram-negative bacilli. The provision of an oral strip enables such drug to be contacted directly with the sites of inflammation. Still other strips contain an effective amount of metronidazole, which targets obligate anaerobes. In preferred embodiments, ciprofloxacin and other similar drugs that target facultative anaerobes—*Staphylococcus, Corynebacterium*, enteric GNRs, etc. are not employed. The use of strips as described herein is a local delivery method to administer antibiotics and offers a novel approach to the management of periodontal "localized" infections. One of the primary advantages is that smaller doses of topical agents can be delivered inside the gingival pocket, avoiding the side effects of systemic antibacterial agents, while increasing the exposure of target microorganisms to higher concentrations and therefore more therapeutic levels of the medication. In still other embodiments, strips are impregnated with zinc salts as they are non-toxic and do not stain teeth compared with other metal salts. The zinc is believed to assist in the inhibition of growth of undesired bacteria in the oral cavity. Moreover, in other preferred embodiments, strips include explicitly exclude, e.g. are devoid of, either manganese or cooper, as it is known that spirochetes use the same, instead of iron.

Another approach to antimicrobial therapy in the control of infection associated with periodontitis is the concept of full mouth disinfection. In certain embodiments, this is employed in concert with subsequent oral strip use. The procedure consists of full mouth debridement and the brushing of the tongue with chlorhexidine gel and then the mouth is rinsed with chlorhexidine solution so that periodontal pockets are irrigated with chlorhexidine solution. Chlorhexidine rinses are preferred and continued for several weeks to aid healing and augment plaque control. Systemic administration of doxycycline with full mouth disinfection is designed to result in better improvement of periodontal parameters and elimination/suppression of putative periodontal pathogens. Prior to or in association with the oral strip, repopulation of the mouth with beneficial bacteria, and preferably those found in healthy Amish individuals, is believed to be the most effective way to maintain oral health in a manner that will prevent later Alzheimer's disease.

Periodontitis is basically a result of inflammation caused due to wide array of pathogenic microorganism. These microorganisms release numerous proteolytic enzymes, resulting in destruction of soft and hard tissues supporting the teeth. Protease or peptidase is one of the major virulence factors of *Prevotella intermedia*. Besides its role in degrading the host tissue, proteolysis is also an important part of the signaling pathway involved in various pathologies including inflammatory diseases.

In certain embodiments the integrity of the gum tissue of an individual human being is improved by contacting the tissue with an effective amount of a composition comprising one or more sources of zinc ions, which may involve compositions comprising zinc or zinc salts. In addition, certain amino acids are preferably also provided, especially arginine, asparagine, and preferably the pH of the oral cavity is maintained for at least 1 hour at a pH below 6.5.

In still other embodiments, a prebiotic composition is employed to treat various diseases and conditions, such as allergies and infections by pathogenic bacteria. Preferably such prebiotic includes L-arginine to combat the formation of biofilms of other bacteria and includes food sources for beneficial bacteria to thrive, such bacteria including *Veillonella* and *Streptococcus*.

One aspect of the present invention is directed to a microorganism that binds to *Streptococcus pyogenes*, preferably such microorganism being a lactic acid bacterium. In an especially preferred embodiment, the microorganism or the analog, fragment, derivative, mutant or combination thereof, belongs to the *Lactobacillus* genus and in other preferred embodiments, the microorganism or analog, fragment, derivative, mutant or combination thereof does not have the ability to coaggregate with commensal microorganisms of the mucous membranes. Such a microorganism is preferably selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum, Lactobacillus ingluviei* or analogs, derivatives, fragments or mutants thereof.

Preferred products for application of various compounds and substances of the present invention include, in addition to the preferred use of strips as described herein, toothpaste, mouth washes, gargle solutions, nose sprays, mouth sprays, throat sprays, chewing gum, hydrogel, creams, etc.

The preferred composition is for topical prophylaxis or treatment of microbial diseases of inflammatory diseases of the oral cavity. It is preferably for use in prevention or treatment of microbial diseases of the oral cavity but can also be used for topical prevention or treatment of microbial diseases or inflammatory diseases.

In still other embodiments, oral compositions are employed that include tomatidine, separately or in addition to the other compositions set forth herein, including L-arginine, xylitol, zinc ions, and preferred beneficial bacteria. The amount of tomatidine administered is preferably at least about 10 micro-mole, and more beneficially with between about 25 micro-mole and 50 micro-mole. Moreover, administration of tomatidine is believed to increase the production in an individual of amounts of certain amino acids, such as free amino acids of leucine, threonine, tryptophan, arginine, histidine, valine, isoleucine, and methionine.

Many biochemical, pharmacological, neuropathological, and experimental data suggest a role of nitric oxide in the pathogenesis of neurodegenerative diseases, as well as headaches and migraines. Nitric oxide (NO) is a very important molecule in the regulation of cerebral and extra cerebral cranial blood flow and arterial diameters. It is also involved in nociceptive processing. Glyceryl trinitrate (GTN), a prodrug for NO, causes headache in normal volunteers and a so called delayed headache that fulfils criteria for migraine without aura in migraine sufferers. One aspect of the present invention is to prevent migraines via the inhibition of NO production; the blockade of steps in the NO-cGMP pathway; or the scavenging of NO. The pain signaling molecules, nitric oxide synthase (NOS) and calcitonin gene-related peptide (CGRP) are implicated in the pathophysiology of migraines. Nitric oxide synthases (NOSs) play an essential role in synthesizing nitric oxide (NO) by oxidizing 1-arginine.

Non-specific NOS inhibition and a specific neuronal NOS inhibitor have been found to attenuate neurogenic dural vasodilation. Interestingly, specific inducible and endothelial NOS inhibitors had no effect. Non-vascular inducible NOS inhibitors have been shown unable to abort or prevent migraine. Neuronal NOS inhibition and bacterial NOS inhibition (bNOS) are useful for therapy, with the latter being considered the primary causative agents in preventing migraines. Neurons in the trigeminocervical complex are the major relay neurons and are the neural substrates of head pain. NO production in the TCC and potentially other areas of the brain may be involved in triggering migraines, and therefore blocking NO production is believed to be therapeutic. The biological nitrogen cycle involves step-wise reduction of nitrogen oxides to ammonium salts and oxidation of ammonia back to nitrites and nitrates by plants and bacteria. The salivary bacterial reduction of nitrate to nitrite has been recognized as an important metabolic conversion in humans. Several enteric bacteria have also shown the ability of catalytic reduction of nitrate to ammonia via nitrite during dissimilatory respiration.

The nitric oxide synthase inhibitor NG-monomethyl-L-arginine (L-NMMA) may be employed in several embodiments of the present invention. For example, blockade of nitric oxide synthases (NOS) by L-NMMA effectively treats attacks of migraine without aura. Similar results have been obtained for chronic tension-type headache and cluster headaches.

Nitric oxide synthases (NOSs) are multidomain metalloproteins first identified in mammals as being responsible for the synthesis of the wide-spread signaling and protective agent nitric oxide (NO). Nitric oxide synthases are heme-based monooxygenases that oxidize L-arginine to nitric oxide (NO), a signaling molecule and cytotoxic agent in higher organisms. NO is one of the main inflammatory mediators involved in both inflammation and angiogenesis. NO can be synthesized by three different isoforms of NO synthase: neuronal (nNOS), endothelial (eNOS), and inducible (iNOS) synthases. NO production due to cytokine-induced expression of inducible nitric oxide synthase (iNOS) is largely involved in the pathophysiology of inflammation.

Although NOS-like activity has been reported in many bacteria, only a few bacterial homologs of mammalian NOSs (mNOSs) have been characterized to date. Nitric oxide synthases (NOSs) play an essential role in synthesizing nitric oxide (NO) by oxidizing 1-arginine. NO is a significant mediator in cellular signaling pathways. It serves as a crucial regulator in insulin secretion, vascular tone, peristalsis, angiogenesis, neural development and inflammation. Due to its important role, the inhibition of these vital enzymes provides therapeutic applications that target NOSs.

Prokaryotic proteins homologous to animal NOSs have been identified and characterized, both in terms of enzymology and biological function. In contrast to mNOSs, which possess both a catalytic and a reductase domain, the bacterial enzymes lack reductase domains and require the supply of suitable reductants to produce NO. A notable exception is a NOS from a gram-negative bacterium that contains a new type of reductase module. Bacterial NOSs seem to have functions that differ from those of mNOSs, including nitration of different metabolites and protection against oxidative stress.

In one embodiment, the lactic acid bacterium *Lactobacillus reuteri* is employed as it is believed that by doing so, one is able to induce oxytocin, preferably in a manner that offers a sustained induction of oxytocin, unlike the short effects achieved using intranasal oxytocin sprays, etc. Thus one aspect of the present invention relates to the employment of probiotics-induced oxytocin to reduce certain disease symptoms, as well as headaches, especially in the form of an oral administered compositions, such as via adhesive strips, mouthwashes or toothpaste.

Formulation of oral drug strips involves the application of both aesthetic and performance characteristics such as strip-forming polymers, plasticizers, active pharmaceutical ingredient, sweetening agents, saliva stimulating agent, flavoring agents, coloring agents, stabilizing and thickening agents. From the regulatory perspectives, all excipients used in the formulation of oral drug strips should be approved for use in oral pharmaceutical dosage forms. For example, films that incorporate a pharmaceutically active ingredient are disclosed in expired U.S. Pat. No. 4,136,145 to Fuchs, et al. These films may be formed into a sheet, dried and then cut into individual doses.

With respect to manufacturing of strips, one of skill in the art will appreciate the various methods and components involved to achieve desired qualitative and quantitative aspects. For example, if a dissolvable strip is intended to last over a several hour period, the changes in content of materials used in the manufacture, for example, of breath strips, can be adjusted to lengthen the time it takes to dissolve such strip. Flavor, binding and adhesion abilities, etc. are adjusted suitably to achieve desired results. Thus, while the present specification provides some detail as to how to make and use certain embodiments of the present invention, reliance on incorporation by reference is appropriate to encompass the myriad of ways in which a particular product is produced. All of such techniques, however, are well within the skill of one of ordinary skill in the art in view of the guidance and direction provided herein.

Preferably the strips of the present invention are made in a manner that do not dissolve in fewer than ten seconds, thus distinguishing the same from common breath strips widely available. The strips of the present invention may have a weight of from 30 to several hundred mg, preferably over 33 mg. Preferably, strips of the present invention have sufficiently high moisture content to impart the product with flexibility and to avoid becoming brittle, e.g. the strips should preferably avoid cracking when bent.

In certain embodiments, the methods employed by Mono-Sol Rx with respect to a thin film drug delivery technology can be used, preferably providing a strip having a relatively thin film, which is similar in size, shape and thickness to a postage stamp. Preferably, the strips of the present invention, when containing active ingredients, have the ability to carry doses of prescription products up to 80 mg or exceeding 1000 mg, and even more preferably, over 200 mg. Suitable taste masking agents can be employed depending upon the active ingredients involved.

Other embodiments of the present invention are directed to multiple film laminates that can have distinct adherence and qualitative features and components associated with separate layers, thus facilitating differences in manufacture, activity, structural characteristics, such as flexibility, dissolution rate, etc. The strips of the present invention provide the requisite pliability and tensile strength necessary to securely adhere to a person's mucosal tissues for at least one hour, more preferably at least two hours, and even preferably a bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts.

In other embodiments, to achieve the desired thickness of strips for structural support purposes of the present invention, a so-called slab or sheet manufacturing technique is employed that uses a nonaqueous, extrudable composition comprising at least one thermoplastic polymer in an amount of more than 20 wt % of the whole composition, such composition comprising at least one thermoplastic polymer and one or more bioactive ingredients in a form that may be placed on the mucosa and having an average dissolution time of preferably more than 50 minutes, more preferably at least about 2 hours, and even more preferably at least about 5 hours. In some embodiments the strip is in a sheet and has a surface area of approximately 0.25-1.5 in. and a thickness of approximately 10-70 mil. A strip may be impregnated or coated with a dose of active ingredient and other components. Preferably, strips of the present invention comprise a mixture of at least three types of film forming agents, such as maltodextrins, fillers (for example, microcrystalline cellulose (MCC)) and hydrocolloids (for example, sodium aliginate), suitably adapted to adhere to oral surfaces of an oral cavity, and in particular the soft palate. While structural support for the soft palate is the principal direction of the present invention, embodiments also comprise the use of such strips to deliver or release oral care agent(s). Such agents include anti-microbial agents and salivary stimulants to treat, for example, halitosis, dental plaque, gingivitis, xerostomia, dry mouth, like oral conditions or combinations thereof. Further, the oral care edible film can act as a breath freshener effective against malodor. In other embodiments, both a longer acting (if not entirely non-dissolvable strip) can be employed in association with one or more other strips having other desired characteristics. For example, a structural support strip can be used to achieve breath freshening, delivery of a medicinal compound, etc.—with such second strip having entirely distinct dissolution characteristics.

Thus, in one embodiment, an oral care product comprises a thin film oral strip that adheres to the mucosal membrane, (e.g. the buccal membrane of a person's mouth) for a period of at least 1 hour and more preferably up to 3 hours, such strip provided with elements, compounds or compositions that address one or more long felt but unsolved issues with a human being's oral cavity, e.g. halitosis; dry mouth, etc. As opposed to and in contrast with thin film strips that almost immediately dissolve in one's mouth, certain embodiments of the strips of the present invention are structured, configured and adapted for far longer period=s of time within which they will dissolve in the oral cavity, thus providing longer term durations within which to address halitosis or dry mouth conditions. As set forth herein, the size of such strips can vary, but are preferably sized to attach to the side of one's mouth much like a postage stamp size, thus avoiding undue steric interference with one's tongue, etc. In some embodiments, the strip is adapted to be secured directly to one's tongue, either on the top or bottom surface thereof, and in other embodiments, adapted to adhere to tissue just below the tongue. The particular provision of such strips with selected beneficial bacteria and/or prebiotics, probiotics, etc., satisfies a need to address the certain population of bacteria in one's mouth that could otherwise promote bad breath, such as sulfur producing bacteria. In certain embodiments, the strips for one's oral cavity comprise *Rothia* bacteria. In other embodiments, they include *Streptococcus salivarius* bacteria. In others, they include a combination of bacteria adapted to thereby form beneficial biofilms where a variety of beneficial bacteria prosper due to their symbiotic relationship with each other due to the production by one or more of such bacteria of metabolites or other elements that another species of bacteria employs as a nutrient for growth and maintenance.

The oral cleansing and breath freshening effects of the edible film of the present invention can be achieved by entrapping the oral care agents within the oral cavity to provide extended efficacy. In this regard, the highly dissolvable edible film can act as a medium through which a pharmaceutically active oral agent can be administered via a mucous membrane of the oral cavity—but with a duration of adhesion to a mucosal membrane such that extended beneficial periods of time elapse over which compositions, bacteria, nutrients, vitamins, etc. are delivered through the oral cavity tissues, rather than relying upon a pill form that must survive the rigors of the intestinal tract.

Strips may further include a variety of other suitable ingredients, such as softeners, colorants, flavoring agents, emulsifiers, surface active agents, thickening agents, binding agents, sweeteners, fragrances, other like ingredients or combinations thereof.

In still other embodiments, the oral compositions can address the loss of teeth by individuals, including the prevention of such tooth loss or the prolonging of the presence of teeth until a later age of the individual. Tooth loss is particularly common with individuals who have periodontitis, and thus, employment of various embodiments of the present invention address tooth loss by combating periodontitis by reducing the population of pathogenic bacteria that cause such disease, and by fostering the populations of beneficial bacteria in a person's oral cavity.

In some embodiments of the invention, bacteria are employed in oral compositions, preferably via thin film strips that adhere to buccal membranes for at least 1-3 hours, and that include beneficial bacteria that reduce the amount of available sugars that would otherwise be consumed by pathogenic or cavity causing microbes and bacteria. Thus, one feature of certain embodiments includes the ability to fight cavity formation by reducing the level of sugars that are used by cavity causing microorganisms, with such reduction effected by the purposeful increase of a population of selected bacteria that employ the same sugars to promote growth and maintenance. Therefore, there is a competitive inhibition of undesired bacteria by purposefully populating one's oral cavity with more beneficial bacteria that cause far less cavity formation than other bacteria normally present in a person's mouth.

In certain embodiments, oral probiotic strains that include at least *Streptococcus salivarius* are included in compositions in a manner to support natural immune defenses by preventing infections of the oral cavity, such infections including those associated with pathogenic bacteria that cause infections, such as tonsillitis, pharyngitis and ear infections, as well as those that cause gum disease and plaque build-up on human teeth.

The oral cleansing and breath freshening effects of the oral compositions, especially the thin film strips, of the present invention can be achieved by entrapping the oral care agents within the oral cavity to provide extended efficacy. Such oral compositions, especially in the form of film strips, may thus act as a medium through which a pharmaceutically active oral agent can be administered via a mucous membrane of the oral cavity. Oral compositions and strips may further include a variety of other suitable ingredients, such as softeners, colorants, flavoring agents, emulsifiers, surface active agents, thickening agents, binding agents, sweeteners, e.g. Xylitol, fragrances, other like ingredients or combinations thereof as set forth herein, designed for a slow release to address halitosis and dry mouth conditions.

Preferably such oral compositions and/or strips are applied in an environment where the pH of saliva is adjusted to be below 6.5, which is believed to be a level where spirochetal activity is often observed. Most spirochetes are free-living and anaerobic. The strips themselves may be adapted to reduce the pH of the oral cavity. While an acidic pH seems to favor certain bacteria, specifically most aerobic bacteria and alkaline pH levels seem to advance anaerobic bacteria growth, one aspect of the present invention is to provide a strip that is able to adjust the pH of an individual's oral cavity to address particular situations so as to favor the growth of certain bacteria over others. Acidosis (an acidic condition of the body) reduces available oxygen to the cells and can contribute to the increased presence of certain bacteria. Certain embodiments of the present invention are therefore directed to the purposeful infection of a person with spirochetes bacteria that have been treated with a CRISPR-Cas system to render them sensitive to antibiotics or to otherwise make them vulnerable in a fashion such that they are rendered far easier to control or kill. The competitive inhibition of other similar bacteria that possess virulence factors can be employed to reduce the number of pathogenic bacteria in a person's oral cavity.

As an additional step in various methods set forth, tongue scrapping to remove resident bacteria from a human being's tongue can be performed prior to administration of the oral compositions/strips set forth. The brushing of the tongue with chlorhexidine gel and/or rinsing the mouth with chlorhexidine solution is also a preferred pre-step.

Antimicrobials have been used extensively as growth promoters in agricultural animal production, but the specific mechanism of action for them has not yet been determined. Tylosin administration has been found to decrease the proportion of bacteria in the phyla Bacteroidetes, of which *Prevotella* is a member. Despite widespread use of antibiotics for the treatment of life-threatening infections and for research on the role of commensal microbiota, our understanding of their effects on the host is still very limited. Several studies have demonstrated that tetracyclines, the antibiotics most intensively used in livestock and that are also widely applied in biomedical research, interrupt mitochondrial proteostasis and physiology in animals ranging from round worms, fruit flies, and mice to human cell lines.

Prophylactic low-dose antibiotics administered to livestock populations result in an increase in the rates of growth and weight gain, prompting their widespread use as agents to promote growth in commercial animal herds. Although some of this effect is likely due to changes in the gut microbiome, some believe that these effects result from a low-level increase in the release of mitochondrial ROS. Low levels of mitochondrial ROS are essential for cellular proliferation, differentiation, and metabolic adaptation.

In particular embodiments, the use of CRISPR systems to target virulence factors of bacteria, and in particular, *Prevotella* is employed to enable the maintenance and/or destruction of particular microbial populations when desired. For example, some of the virulence factors that may be targeted include the following: Gingipain; Capsular polysaccharide; fimbriae; etc. and the employment of CRISPR-Cas systems are used to reduce the virulence factors thereof. While antibiotic therapy is non-discriminatory in its action, the use of CRISPR systems permits one to fine tune the selective elimination of particular microbes. One survival mechanism of *Prevotella* cells is the possession of natural antibiotic resistant genes, which prevent extermination. Modification of *Prevotella* using a CRISPR-Cas system, provides a way to render *Prevotella* susceptible to antibiotics, thus permitting its regulation. Certain antibiotics found useful in treating *Prevotella* include metronidazole, amoxycillin/clavulanate, ureidopenicilins, carbapenems, cephalosporins, clindamycin, and chloramphenicol.

One aspect of many embodiments of the present invention include the use of specialized viruses to supply CRISPR/Cas to rid bacteria of antibiotic-resistance plasmids and/or other virulence factors. Virulence factors of Gram-negative anaerobes such as *Prevotella* include, for example, fimbria, hemolysins, adhesions and hemagglutinins. These bacteria commonly produce immunoglobulin-degrading enzymes and some produce tissue-degrading enzymes. Additionally, bacteria of the genus *Prevotella* are often resistant to antibiotics, such as tetracycline, erythromycin, and .beta.-lactam antibiotics. In practice, a *Prevotella*-targeting lambda phage is created that encodes the CRISPR genes plus spacers that target two conserved .beta. lactamases, enzymes that confer resistance to .beta.-lactam antibiotics. Once integrated into the *Prevotella* genome, the phage prevents the transfer of .beta. lactamase-encoding plasmids and can also delete these plasmids from individual bacterial cells. These lambda phage-encoding bacteria then become sensitive to treatment with antibiotics.

In one embodiment, an antibacterial rinse is employed, such as that described in U.S. Pat. No. 8,496,914 to Bonfiglio, and such method comprises rinsing with an antibacterial oral rinse formulation for a period of time immediately prior to engaging in oral hygiene activities. After effectively killing a majority of *Prevotella* in a person's mouth, the person reestablishes a population of *Prevotella* in their mouth by swishing their mouth with a solution containing *Prevotella* bacteria that have been modified as described herein. In certain embodiments, virulence factors that are targeted include proteins involved in host cell attachment and invasion (e.g., fimbriae and adhesins), cytotoxicity (e.g., hemolysins and toxins), iron-acquisition (e.g., siderophores) and evasion or disruption of host-cell defenses (e.g., capsule). Genes encoding these factors have been shown to be linked to plasmids and the distinct chromosomal regions that are termed pathogenicity islands.

In various embodiments of the present invention, bacterial DNA is altered from pathogenic to non-pathogenic using various methods known to those of skill in the art. One such method is the employment of a CRISPR-Cas system to introduce a mutation to the bacterial genome, and particularly to a *Prevotella* bacterium, including to specific genes encoding for membrane or secretory products, and/or other genes that regulate virulence genes. Interference with the expression or efficacy of various pathogenic characteristics of certain bacteria, such as by affecting particular virulence factors possessed by bacteria, viruses, fungi, and protozoa, including but not limited to immunoglobulin (Ig) proteases, capsules, endotoxins, mobile genetic elements, plasmids, and bacteriophages. Specifically, and to provide representative examples, virulence factors for *Staphylococcus aureus* include hyaluronidase, protease, coagulase, lipases, deoxyribonucleases and enterotoxins. For *Prevotella*, proteins involved in adherence to surfaces and/or other cells are modified to reduce competent biofilm formation. Examples for *Streptococcus pyogenes* are M protein, lipoteichoic acid, hyaluronic acid capsule, destructive enzymes (including streptokinase, streptodornase, and hyaluronidase), and exotoxins, including streptolysin. Examples for Listeria monocytogenes include internalin A, internalin B, lysteriolysin O, and actA. Examples for Yersinia pestis include an altered form of lipopolysaccharide, and YopE and YopJ pathogenicity. Other virulence factors include factors required for biofilm formation (e.g. sortases) and integrins (e.g. beta-1 ad3). In addition to bacteria, helminthes possess similar factors, such as neutrophil inhibitory factor. Thus, one aspect of the present invention is to employ CRISPR systems to achieve interference with specific virulence factors or with regulatory mechanisms that control the expression of multiple virulence factors, and in such a manner, provide a way for such microbes to positively affect a person's immune system without attendant pathogenicity. In certain embodiments this may take the form of employing CRISPR loci to control, for example, the dissemination of antibiotic resistance in bacterial species, such as staphylococci. For example, CRISPR targeting of *Streptococcus pneumoniae* capsule genes, essential for pneumococcal infection, provides a way to thwart bacteria virulence and pathogenic effects. In certain embodiments, the CRISPR-Cas systems are effectively employed as a regulator of gene expression and in such manner, provides a way for bacteria, especially pathogenic bacteria, instead of being eliminated by the use of broad based antibiotics, are transformed into non-pathogenic microorganisms, thus maintaining the positive attributes that they provide in a microbiome of an individual.

Figure 4:
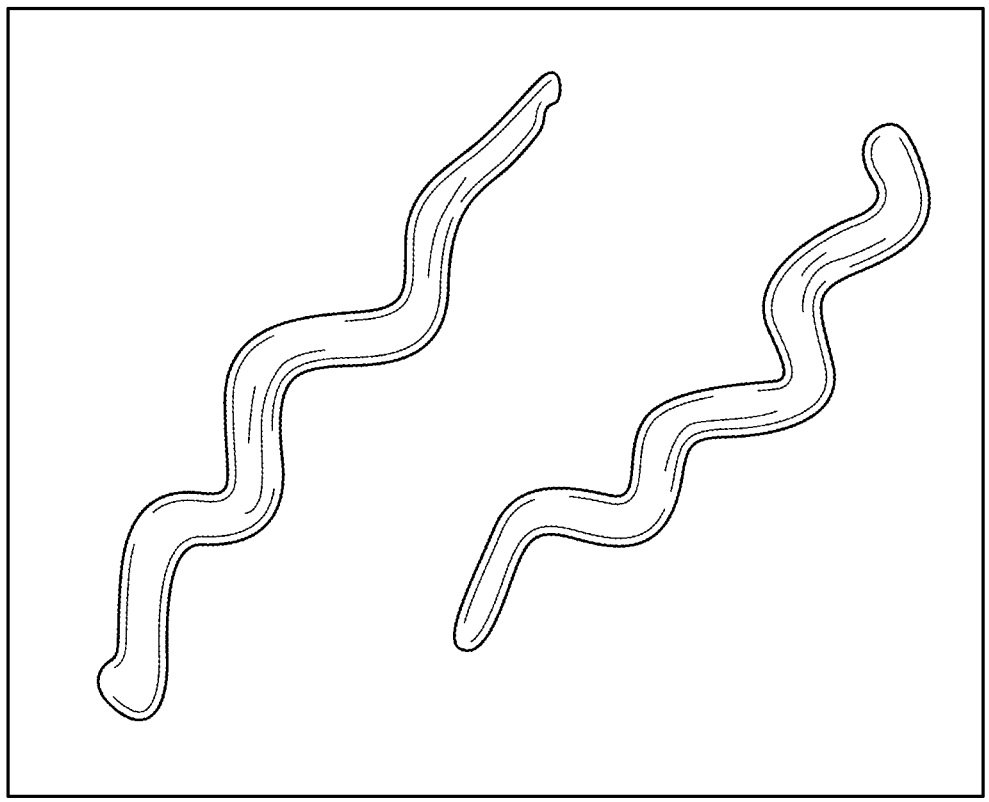
FIG. 4 shows close up views of spirochetes, illustrating their spiral nature and conformation.

FIG. 4 shows close up views of spirochetes, illustrating their spiral nature and conformation. Typical applications and administration techniques of antibiotics may not eliminate oral spirochetes as in other spirochetal diseases, such as syphilis. Typical administration of antibiotics is believed to only force the spirochetes into a more protected spore form, thus triggering a survival strategy that allows them to resurface at a later date. One aspect of the present invention is therefore directed to effective administration of an antibiotic that will effectively reduce the population of spirochetal microbes that are causative of Alzheimer's disease via the direct application of antibiotics via oral mucosal adhesive strips. Preferably such strips are applied in an environment where the pH of saliva is adjusted to be below 6.5, which is believed to be a level where spirochetal activity is often observed. Most spirochetes are free-living and anaerobic. The strips themselves may be adapted to reduce the pH of the oral cavity. While an acidic pH seems to favor certain bacteria, specifically most aerobic bacteria and alkaline pH levels seem to advance anaerobic bacteria growth, one aspect of the present invention is to provide a strip that is able to adjust the pH of an individual's oral cavity to address particular situations so as to favor the growth of certain bacteria over others. Acidosis (an acidic condition of the body) reduces available oxygen to the cells and can contribute to the increased presence of certain bacteria. Certain embodiments of the present invention are therefore directed to the purposeful infection of a person with spirochetes bacteria that have been treated with a CRISPR-Cas system to render them sensitive to antibiotics or to otherwise make them vulnerable in a fashion such that they are rendered far easier to control or kill.

Figure 5:
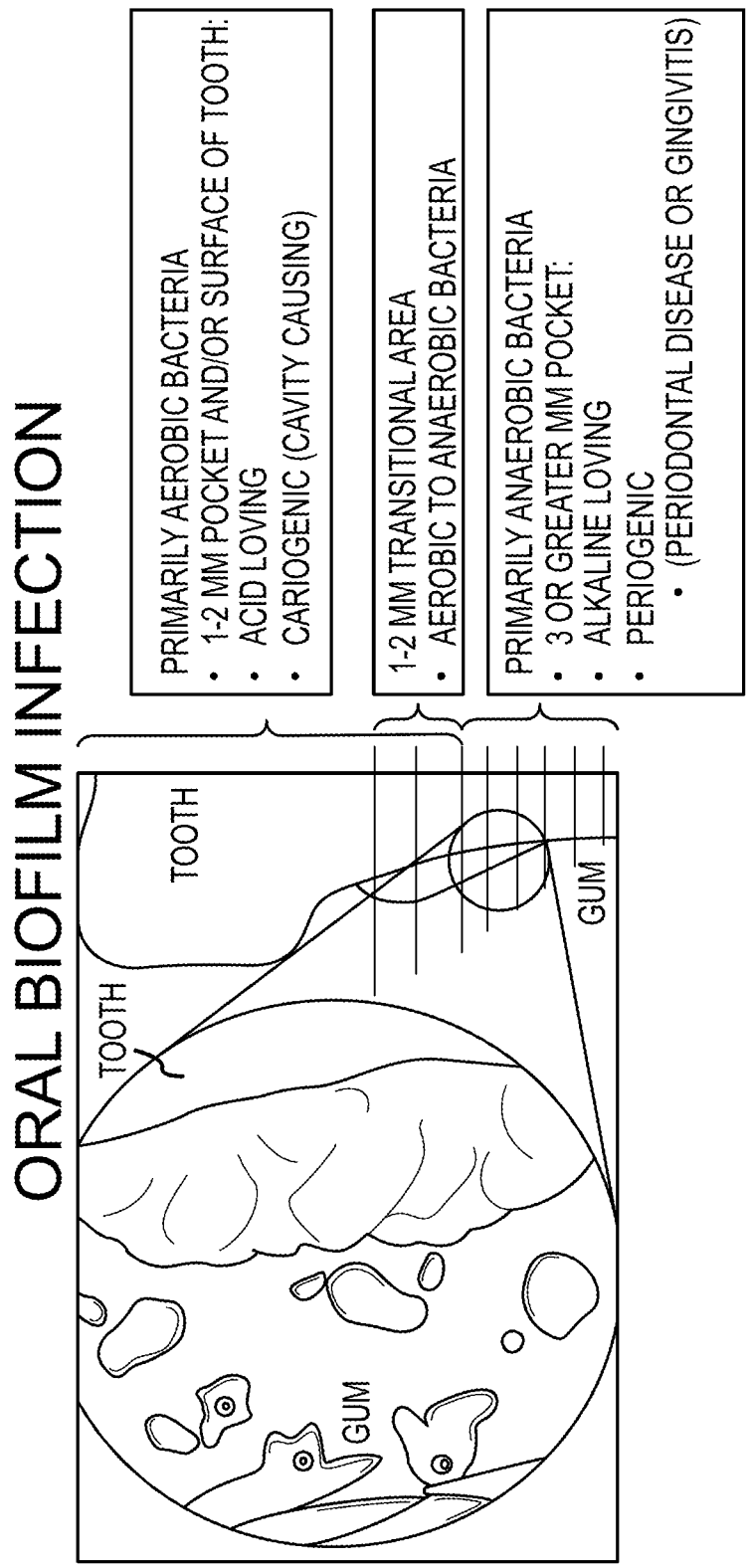
FIG. 5 illustrates oral biofilm infections of the human body, showing a human tooth, gum and the sites of periodontal disease.
Figure 6:
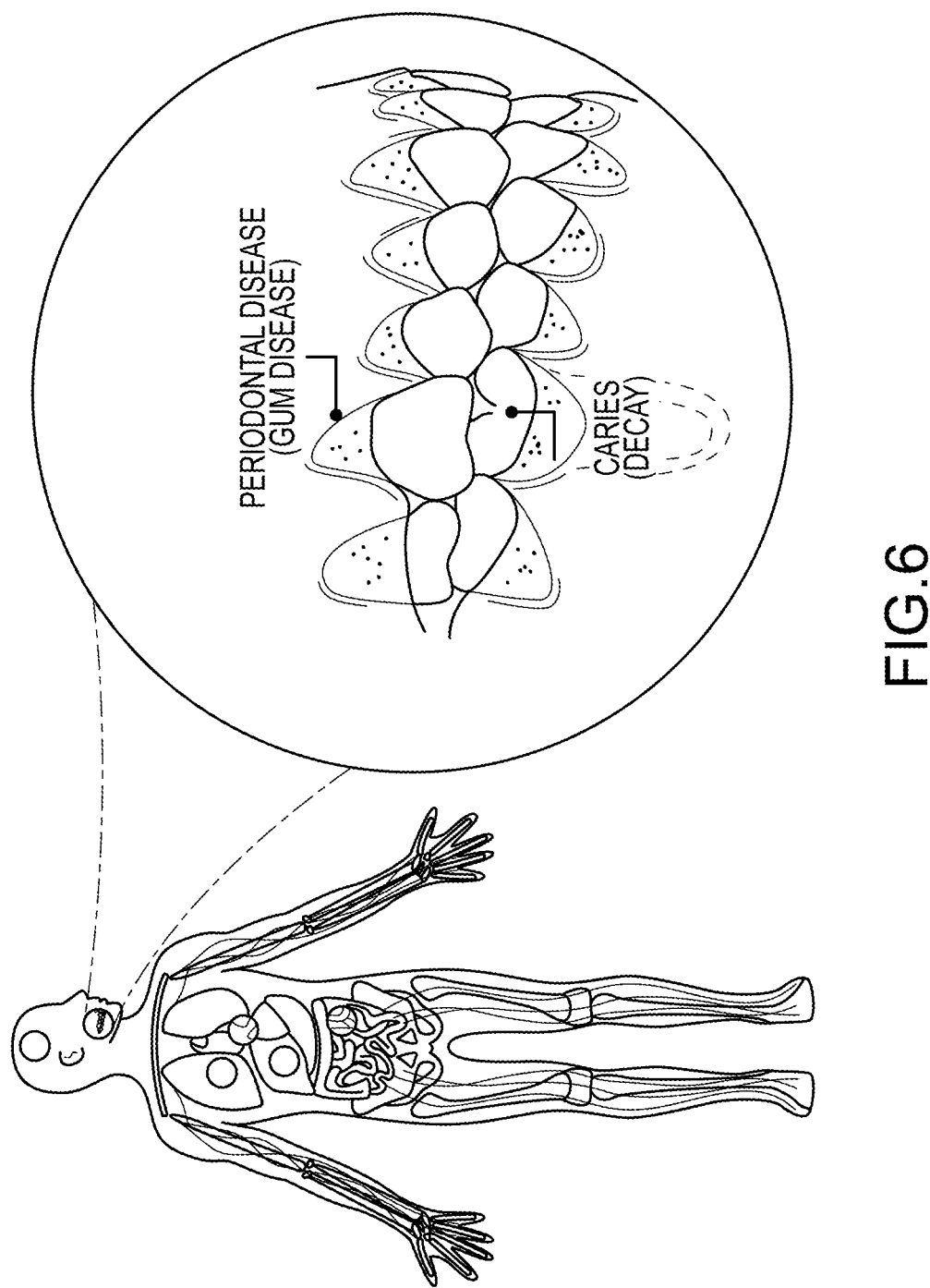
FIG. 6 illustrates a site of periodontal disease and to areas of the human body believed to be causally affected by inflammation and bacterial infections stemming therefrom.

FIG. 5 illustrates oral biofilm infections of the human body, showing a human tooth, gum and the sites of periodontal disease. Recent reports have documented that infectious agents also occur in atherosclerosis, cardio- and cerebrovascular disorders, diabetes mellitus, chronic lung and inflammatory bowel diseases, and various neurological and neuropsychiatric disorders. As the focus of the present disclosure is admittedly on Alzheimer's disease, one of skill in the art will nevertheless appreciate that there is a wide over-lap of the fundamental mechanisms involved in the treatment of Alzheimer's disease as described herein and that the teachings herein find application in one or more of the above listed conditions, and thus, this specification is intended to and should be considered as encompassing the treatment of such conditions. FIG. 6 illustrates a site of periodontal disease and to areas of the human body believed to be causally affected by inflammation and bacterial infections stemming therefrom.

A paradigm shift in recent years has led to the consideration of the oral cavity as being critically important in maintaining systemic health. A basic difficulty in destroying certain bacteria present in oral biofilms is that they are not actively dividing, which makes them resistant to attack by a large group of antibiotics and antimicrobials that attack the bacteria only during the active parts of their lifecycle, e.g., cell division. Certain bacteria can also form spores, which are hard, non-permeable protein/polysaccharide shells or coatings. Spores provide additional resistance to eradication efforts by preventing attack from materials that are harmful to the bacteria. Thus, one aspect of the present invention is to plan attacks on particular bacteria when they are actively dividing, or alternatively, to employ biocides and antimicrobials that are strongly acidic and/or oxidizing, often involving halogen atoms, oxygen atoms, or both. Common examples include hypochlorite solutions (e.g., bleach), phenolics, mineral acids (e.g., HCl), $H_2O_2$, and the like. Because dosages of such chemicals must be allowed to contact the biofilm or spore for extended amounts of time to be effective, the oral strips as described herein are well suited for this purpose and various embodiments of the present invention are directed to strips that contain one or more of the above described biocides and antimicrobials.

In certain embodiments, especially those directed to strips adapted to address anaerobic bacteria, such strips are provided such that they further generate an environment in the oral cavity that establishes a pH greater than 7 and less than about 10. The strips thus employed are effective at interrupting or breaking ionic crosslinks in the macromolecular matrix of a biofilm, which facilitates passage of desired anti-bacterial agents through the matrix to the bacteria entrained therein and/or protected thereby. Surfactants of known types can further be employed to assist in breaking down biofilms. Using the strips as described, one is able to employ lower concentrations than would be possible in systemic administrations and still achieve the desired break down of the bacterial biofilm. While much of the discussion herein is directed to *Prevotella*, one of skill in the art will understand that other bacteria present in the oral cavity can also be targeted for use in combatting periodontal disease, and thus AD. For example, one of the most studied bacteria implicated in periodontal disease is *F. nucleatum*. It belongs to the Bacteroidaceae family and is a dominant microorganism within the periodontium. It is a gram-negative anaerobic species of the phylum *Fusobacteria*, numerically dominant in dental plaque biofilms, and important in biofilm ecology and human infectious diseases. Dental plaque is a complex and dynamic microbial community that forms a biofilm on teeth, and harbors more than 400 distinct species in vivo. *F. nucleatum* is a prominent component quantitatively and is one of the first Gram-negative species to become established in plaque biofilms. It is a central species in physical interactions between Gram-positive and Gram-negative species that are important in biofilm colonization, and contributes to the reducing conditions necessary for the emergence of oxygen-intolerant anaerobes: it is considered as an intermediate colonizer bridging the attachment of commensals that colonize the tooth and epithelial surface with true pathogens. *F. nucleatum* is one of a small number of oral species that is consistently associated with, and increased in number at, sites of periodontitis, one of the most common infections in humans. *F. nucleatum* has been shown to be a potent inducer of collagenase 3 (MMP-13) production. This suggests that *F. nucleatum* may be involved in the pathogenesis of periodontal diseases by activating multiple cell signaling systems that lead to stimulation of collagenase 3 expression and increased migration and survival of the infected epithelial cells. By eliminating immune cells that are important for immune defense against oral bacteria, *F. nucleatum* can contribute to the recruitment of other pathogenic bacteria and subsequently to the initiation and the progression of periodontal disease. Indeed, positive association between *F. nucleatum, P. gingivalis* and *P. intermedia* and *Bacteroides forsythus* in sub-gingival plaque samples has been reported. Colonization by *P. intermedia* was found to be due to *F. nucleatum*, since *P. intermedia* is not detected in a site unless *F. nucleatum* was also present. It is believed that *F. nucleatum* recruits and activates local immune cells, resulting in tissue destruction and the progression of periodontal disease. Instead of debating whether *F. nucleatum* is commensal or pathogenic, one aspect of the present invention is to employ CRISPR-Cas systems to modify such bacteria to advantageously affect various virulence factors of such bacteria so as to better address access to biofilms where other bacteria, such as spirochetes, reside, thus providing a way to reduce the incidence of AD. *F. nucleatum* has periodontopathogen properties but also appears to be a very sensitive microorganism such that it can be targeted with respect to its coaggregation properties, thus allowing one of skill in the art to interfere with biofilm formations involving this bacterium and interfering with its abilities to transport and interact with other periodontopathogen bacteria.

With a better understanding of how the microbiota interacts with the host's physiology gained in the last few years, one aspect of various embodiments of the present invention is to integrate an individual's microbiota into a form of personalized healthcare so as to treat an individual's diseases more efficiently and in a more targeted fashion. With a more complete understanding of the AD disease process, the manipulation of the oral microbiome is focused on to modulate the otherwise normal course of AD disease progression. While Hippocrates may have been correct that food is medicine and medicine is food—and that all disease begins in the gut—the present inventors believe that before the food arrives at the gut, it must pass through the oral microbiome—and it is in the oral cavity that one can effectively address many of the diseases of the modern era, including AD. Saliva is colorless, odorless and has a relative density of 1.004-1.009 and a pH of 6.6-7.1. Saliva consists of 99% water and the remainder is organic molecules such as salivary amylase, mucopolysaccharide, mucin and lysozymes, and some inorganic matter such as $Na^+$, $K^+$, $Ca^{2+}$, $Cl^-$ and the thiocyanate ion. Levels of nitric oxide (NO) have been detected in saliva and gingival crevicular fluid collected from patients with gingivitis, aggressive periodontitis and chronic periodontitis—as compared to healthy controls. Salivary AM and NO levels distinguished patients with aggressive periodontitis from other groups. In contrast, patients with chronic periodontitis, aggressive periodontitis and gingivitis showed increased levels of NO in the gingival crevicular fluid, and higher levels of NO were found in patients with periodontitis compared with those with only gingivitis.

The microbial conversion of nitrate to nitrite in the oral cavity and the subsequent conversion to nitric oxide is an important factor in combating various diseases. While for many years, the role of nitrate in the human body has been under debate and usually not in favor of nitrate, recently there has been a revaluation of this paradigm. The present inventors submit that the bacterial reduction of nitrate to nitrite in the oral cavity is important in the progression of AD and that there are health benefits to be derived from the oral presence of nitric oxide. While elevated levels of nitrate and nitrite are associated with periodontal disease, this elevation is thought to be a response of the immune system against infection or stress. Under acidic conditions, nitrite is converted to nitric oxide and acts as an antibacterial agent. *P. intermedia* lipopolysaccharide can induce iNOS expression and stimulate the release of NO without additional stimuli. The ability of *P. intermedia* lipopolysaccharide to promote the production of NO is important in the pathogenesis of inflammatory periodontal disease, and thus in the progression of AD. The strips of the present invention in various embodiments provide a way to provide a potent inhibitor of biofilms that are implicated in periodontal disease, with proper application thereof being effective to provide subgingival margins with anti-periodontal pathogen capabilities so as to combat endodontic biofilms.

Other aspects of the present invention are directed to the use of commensal bacteria to thwart the growth and development of biofilms that are believed to be involved in the progression of AD. Hydrogen peroxide production by commensal is believed to be a major mechanism of inhibition and various species of *Streptococcus* bacteria are employed in certain embodiments of the present invention to inhibit the growth of pathogens. Trace mineral micronutrients are also imperative for optimum host health and balanced levels of trace minerals like iron (Fe), zinc (Zn), selenium (Se) and copper (Cu) are essential to prevent progression of chronic conditions like periodontitis. Their excess as well as deficiency is detrimental to periodontal health. This is specifically true in relation to Fe. Furthermore, some trace elements, e.g. Se, Zn and Cu are integral components of antioxidant enzymes and prevent reactive oxygen species induced destruction of tissues. Their deficiency can worsen periodontitis associated with systemic conditions like diabetes mellitus. In various embodiments of the present invention, the employment of bacteria that is able to generate desired levels of hydrogen peroxide are used to adjust the population of an individual's oral bacteria populations.

While the focus of the present invention is admittedly directed to AD, other diseases are also related to the health of the oral microbiome. For example, arteriosclerosis and arthritis. In many host tissues, including the endothelial lining of blood vessels, produce hsp60 as they respond to certain stressors like high blood pressure. It is postulated that an autoimmune mechanism in which the host responds to foreign hsp60, such as bacterial hsp, could be important in the development of an undesired formation of a lipid-containing material on the endothelial lining of arteries. It has been found that inflamed gingival tissues of periodontal patients exhibit a positive antibody response to both the hsp produced by oral bacteria (e.g. *Porphyromonas gingivalis*) and to human hsp60. This reveals that oral bacteria not only play a role in periodontal disease, but also are involved in diseases related to humoral immune mechanisms. For example, antibodies against the hsps of *P. gingivalis* react with human hsps exposed on the endothelium and produce cellular damage.

Similarly, the destruction caused by the inflammatory pathway when a transient infection becomes chronic demonstrates that the treatments employed to address a transient infection can literally turn the body against itself when the inflammation becomes chronic. The role of chronic inflammation, and in particular periodontitis and its association with many of today's most prevalent diseases, such as cardiovascular disease, Alzheimer's, cancers, diabetes and autoimmune disorders, is at the heart of the various embodiments of the present invention. Coronary Artery Disease remains the number one cause of death in the world. While traditional risk factors partially account for the development of Coronary Artery Disease, chronic inflammation plays a role in the development and propagation of this disease. As a further example, Autism spectrum disorder (ASD) affects a significant number of individuals worldwide with the prevalence continuing to grow. It is becoming clear that a large subgroup of individuals with ASD demonstrate abnormalities in mitochondrial function. Given the ties between microbes and mitochondria, the use of particular antibiotics to kill microbes must also be considered as to the affect such drugs have on mitochondria and the impacts on various disease states such as ASD.

In various embodiments, an oral composition and/or strip that achieves at least two of the following is sought to be accomplished: lower pH; provide NO; provide altered (e.g. reduced virulence factors as compared to native) *Prevotella* or other bacteria, especially pathogenic bacteria such as *P. gingivalis*, and/or interfere with biofilm formation.

In one embodiment of the invention, a method for reducing the likelihood of a Porphyrmonas gingivalis infection in a human being includes adjusting the oral cavity pH of the human being to have a pH of lower than 6.5; reducing the amount of *Fusobacterium nucleatum* in the human being's oral cavity; orally administering to the human being an anti-biofilm agent, as well as a first composition that is effective to either slow down the breakdown of collagen or inhibit the production of collagenase. Preferably such composition includes at least about 200 mg xylitol. Also preferably, the individual is orally administered zinc or a nontoxic zinc salt, as well as a second composition, which may include an antibiotic, provided in an effective amount to reduce the growth of Porphyrmonas gingivalis bacteria residing on the subgingival tooth area of the human being. Such method reduces the likelihood of a Porphyrmonas gingivalis infection in the human being and reduces the virulence factor gingipain. Preferably, the anti-biofilm agent and first and second compositions are provided in one of a mouthwash, an oral strip and/or a toothpaste.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications.

DETAILED DESCRIPTION OF PREFERRED EMBODIMENTS OF THE PRESENT INVENTION

In particular embodiments, the invention is directed toward a preventative treatment for AD involving the provision of an enhanced population of *Prevotella intermedia* bacteria in a person's oral cavity, and more preferably being a population of *Prevotella* that have been modified to make them, one of: more susceptible to antibiotics; altered in their ability to adhere to surfaces, thus negatively affecting their abilities to form biofilms. In preferred embodiments, this is achieved by employing the CRISPR-Cas or CRISPR-Cpf1 systems as described herein. The *Prevotella* bacteria, and in particular *Prevotella intermedia*, as a known pathogen and a major cause of bacteria present in inflammatory periodontal disease, makes it an odd and remote choice for a positive and beneficial bacteria by which to combat AD, and thus, the present inventors believe that this alone provides a teaching away from the use of *Prevotella* by one of skill in the art. While not bound by theory, it is believed that *Prevotella* possesses the beneficial capacity to produce beneficial amounts of nitric oxide (NO) and to foster the expression of inducible nitric oxide synthase (iNOS). Use of especially modified *Prevotella* that reduces biofilm formation is believed to be particularly advantageous as a way to reduce the progression of AD.

One aspect of the present invention is directed to the premise that *Prevotella* is related to Alzheimer's Disease. Clinical and epidemiological studies reveal that the loss of teeth is associated with poor memory. The *Prevotella* bacteria, and in particular, *Prevotella intermedia*, is a known pathogen and a major cause of inflammatory periodontal disease. To achieve the goal of finding a prophylactic treatment for AD, the puzzle contributing to its pathogenesis must be solved and the relationship between oral infection and the etiology of late onset AD discerned. The present inventors believe such puzzle has been solved as described herein.

In the cascade of events causing Alzheimer's disease, oral microorganisms play a significant role, particularly anaerobic bacteria such as *Prevotella* spp. and *Fusobacterium*. The recent observation of microbiome-derived small non-coding RNA (sncRNA) and micro RNA (miRNA) translocation and signaling across endothelial barriers between cells and tissues, indicates that human neurobiology is impacted by the actions of human microbiome-mediated sncRNA and/or miRNA trafficking. The NF-κB signaling pathway for cyto/chemokine release (TNF-315 α, IL-8) produces free radicals, nitric oxide triggers and apoptosis.

In certain embodiments, the present invention is directed to a method for preventing Alzheimer's disease in a human subject who has been diagnosed with periodontitis, involving administering by local gingival application to the subject an effective amount of an antibiotic effective to kill spirochetes bacteria. Preferably, the method includes providing at least 0.5 mg of a bacterial composition that includes *Prevotella* bacteria, and preferrably *Prevotella* bacteria modified to be less adherent to surfaces, thus negatively affecting biofilm formation. as the predominant bacterial genus, such composition administered at least 48 hours after the step of administering the antibiotic that is effective to kill spirochetes bacteria. Preferably administration is via a composition formulated for application directly to a subject's gums and more preferably by the application of a mucosal adhesive strip preloaded with the antibiotic. In one embodiment the antibiotic comprises methotrexate. In other embodiments, the antibiotic comprises doxycycline and methotrexate, with doxycycline provided at a dose of about 20 mg, and even more preferably including a doxycycline pharmaceutical composition that provides steady state blood level of doxycycline of a minimum of about 0.1 µg/ml and a maximum of about 1.0 µg/ml.

Preferably, one or both of the antibiotic and the composition are provided in the form of one of a toothpaste, a mouthwash, a chewing gum, a dental floss, a food product, a gel, a slow-release gel, a tablet, a granule, a film, and most preferrably a dissolvable strip. In certain embodiments, a mucosal adhesive strip contains immunotherapeutic agents effective to treat periodontitis and include a strip impregnated with an agent adapted to locally target anaerobic bacteria at the site of a gum infection and where the agent is provided in an effective amount to kill spirochetes bacteria, preferably adapted to treat an oral environment having a pH of lower than about 6.5.

In one embodiment, a mucoadhesive strip containing immunotherapeutic agents is employed to treat periodontitis, even more preferably a mucoadhesive strip impregnated with an agent of choice to target locally anaerobic bacteria at the site of infection.

Various methods involve a predetermination that the subject is suffering a periodontal disease and is over the age of 40 years old and the composition is effective to kill gram negative anaerobic bacteria. The various methods and systems and compositions are configured to permit an individual to avoid the ravages of Alzheimer's disease and are all directed to preventing the progression of Alzheimer's disease from developing. In still other embodiments, the oral bacterial composition is selected to mimic the oral bacterial composition of healthy Amish individuals. In one such embodiment, in view of the prevalence of oral *Prevotella* by Amish individuals as compared to non-Amish persons, the invention includes the provision of an oral composition containing *Prevotella* on at least a weekly basis, preferably in the form of a lozenge, mouthwash, gum, strip or toothpaste. Such composition is preferably capable of generating nitric oxide in an amount of sufficient to promote oral microbiome health similar to the microbiome health of Amish individuals. As part of certain methods, there is a step of assessing the likelihood that an individual will suffer Alzheimer's disease by analyzing the status of such person's oral health in terms of whether they suffer from periodontitis. Those persons having a diagnosis of periodontitis are then treated with an antibiotic suitable to kill gram negative anaerobic bacteria, specifically an antibiotic regimen effective in substantially eliminating spirochetes from the individual's oral cavity. Preferably, this is via a strip as described herein. Another aspect of the present invention is to determine if a person's oral health reflects a case of gingivitis rather than periodontitis, and in such instance, not administering antibiotics in particular, but rather, a strip with desired bacteria and/or xylitol. The effective administering of antibiotics to address periodontitis may entail a direct topological application, and preferably does not involve a systemic oral administration of an antibiotic due to the localized and specialized nature of oral infections and inflammation of the oral cavity associated with dental plaque.

While not bound by theory, but buttressed by experimental and clinical findings throughout the years, it is submitted that the vast majority of AD is caused by the presence of spirochetes traveling form the oral cavity of an individual, to the person's brain. Once there, the body's immune system reacts by forming amyloid plaques to surround the slow reproducing spirochetes and in the process, causing the havoc that results in the symptoms of AD. It is reflective of the serendipity of life that the causative agent of Alzheimer's Disease has a corkscrew shape. At age 37, after the death of his wife, a formerly rich widow, Alzheimer was financially independent and could indulge in an occasional bottle of wine. Perhaps in some cosmic comedy, Alzheimer's opening of his cherished wines would bring a smile to the Fates contemplating the ironies of life. Spirochetes traverse brain matter by corkscrewing themselves into tissue, only to be eventually enveloped into a sticky goo of amyloid plaque, a spiderman's web designed to stop harm that tragically causes more damage than its original instigator could ever have hoped to inflict. No doubt Alzheimer reminisced about Dr. Gudden, his deceased colleague from their days serving at Frankfurt's Municipal Asylum for the Mentally Ill. Gudden was drowned by Crazy King Ludwig II in an unsuccessful attempt to stop the King's suicide. Alzheimer himself died in 1915 at the age of 51—ironically from a chronic bacterial infection.

It is well known that nitrites are increased in saliva from patients with periodontal disease. In the oral cavity, nitrites may derive partly from the reduction of nitrates by oral bacteria. Nitrates have been reported as a defense-related mechanism. The possibility that the salivary glands respond to oral infectious diseases by increasing nitrate secretion is surmised. Thus, one way to determine whether an individual is a prospect for suffering from Alzheimer's disease is to test whether the saliva of such person has elevated nitrite levels as compared to normal individuals, such as a healthy Amish individual.

In other embodiments of the present invention, the step of determining the presence of spirochetes in the brain of a subject is made prior to the application of medications adapted to address periodontitis. In certain embodiments, an individual at risk of further developing periodontitis is administered doxycycline plus methotrexate, preferably a low dose (about 20 mg) of doxycycline twice daily, and most preferably via a strip as described herein.

One object of the present invention is to provide a mucoadhesive strip that contains a once-daily pharmaceutical composition containing doxycycline that will treat adjacent tissue and reduce anaerobic bacteria and especially spirochetes. Such strips may give steady state blood levels of doxycycline of a minimum of about 0.1 µg/ml and a maximum of about 1.0 µg/ml. Another aspect of the invention is an immediate release strip having a formulation of doxycycline containing less than 50 mg but more than 25 mg, preferably about 40 mg. doxycycline base.

One aspect of the present invention is directed to a method and system that includes providing a person with a composition, particularly one or more oral compositions, that include a collection of bacteria, preferably that include the genus *Prevotella*, that produces nitric oxide to reduce the chances of an individual suffering from Alzheimer's Disease. In certain embodiments, such method and system involve the oral administration of a composition comprising *Prevotella* bacteria capable of producing nitric oxide in a manner such that the person's microflora and bacterial environment in their oral cavity is populated with such *Prevotella* bacteria. Most preferably, the *Prevotella* is attenuated to eliminate one or more virulence factors, such as adherence abilities useful in forming biofilms.

Certain methods provide for preventing the onset or progression of AD by gene editing, e.g., using CRISPR-Cas9 mediated methods to alter genes in *Prevotella* bacteria in order to promote the growth of such bacteria such that increased amounts of beneficial NO are produced. There appears to be a relationship between Nitric Oxide and Alzheimer's disease. Lack of NO production by endothelial cells due to too much ABP aggregate formation and/or free radical generation contributes to the pathology of AD. It is speculated that if NO production could be assured then AD would be significantly halted in its track. NO seems to affect the production of ABP but does not affect its clearance, thus suggesting that NO donors may work as preventative of AD, rather than reversing AD. When NO production was increased by use of a known stimulator of NO production in an animal model of AD, the levels of ABP decreased and there was a significant improvement in memory of animals. Many diseases are characterized by or associated with insufficient nitric oxide production. Experimental and clinical studies demonstrate that insufficient nitric oxide production is associated with major cardiovascular risk factors, such as hyperlipidemia, diabetes, hypertension, smoking and atherosclerosis. Nitric oxide production is also a predictive indicator of future atherosclerotic disease progression. The ability to generate nitric oxide decreases with age resulting in increased risk of heart and vascular disease. Thus, various embodiments are directed to providing beneficial bacteria in the oral cavity that produce NO.

Commensal organisms in the oropharyngeal microbiome may be pathogens or pathogenic under certain circumstances. Healthy individuals commonly harbor low numbers of oral pathogens. The current consensus is that normal commensals may become pathogenic when oropharyngeal dysbiosis is present. Oropharyngeal dysbiosis may arise when various interrelated factors such as diet, salivary flow, pH, immune defenses, and microbial interactions are not kept in balance. Oropharyngeal microbes "seed" the rest of the gastrointestinal tract. It is estimated that 1011 bacterial cells per day flow from the mouth to the stomach. There is a 45% overlap between the oropharyngeal and colonic microbiota suggesting that the oral microbiome strongly influences the composition of the gut microbiome. Pathogenic biofilms in the mouth, if not treated, potentially provide a continual source of pathogenic microbes to the gut. This may contribute to chronic or recurrent stomach, small intestine, or colon dysbiosis.

Inflammatory bowel disease and periodontal disease often present as comorbidities and similar immune pathogenesis have been hypothesized. People with IBD are more likely to have periodontitis than healthy subjects. Patients with IBD and untreated periodontitis have higher opportunistic bacteria populations in inflamed periodontal tissue than those with periodontal disease alone.

Other researchers have commented on the prior research of scientists in the field of AD who have at various times suggested that spirochetes may play a causative role in AD. But confoundingly, such researchers failed to truly appreciate what biologic processes were at issue and therefore, failed to appreciate how to treat AD in a fashion so that it could be prevented. Indeed, while some earlier researchers speculated that spirochetes might play a role in AD, it was thought (incorrectly) that spirochetes may be the source of the beta amyloid deposited in the AD brain. This is believed to have led the majority of researchers to focus efforts, time and money on figuring out ways to address amyloid plaque dispersion, rather than address the root cause of AD. In other words, without a clear understanding of the biological and bacterial interworking of AD, researchers were unable to comprehend in a useful fashion what some earlier clinical results portended. Even with the association between spirochetes infection of a person's brain and the body's own production of amyloid proteins to address such an infection, those of skill in the art failed to appreciate how best to address the situation, as the thick biological barriers prevented the use of drugs that would kill spirochetes. As a result of the confusion reigning in the field, decades have passed where researchers have sought "cures" for AD that were focused on attempts to break down amyloid features. But by doing so, however, there is a risk that the invasive spirochetes will then be released in a fashion that they will cause further damage and harm. In short, even if the current attempts to resolve amyloid buildup in the brain is successful, such an event will not necessarily address the true cause of AD—and indeed, may make things worse for individuals when numerous trapped spirochetes are freed to do further harm.

Still others have simply advocated that the best way in which to treat or prevent AD is to live a healthy lifestyle, adopt behavioral and lifestyle habits that provide good health, eat an avocado instead of potato chips, reduce sugar intake, drink in moderation and quit smoking. The present inventors consider such advice, as well intentioned as it may be, to be utterly unhelpful in addressing the root cause of AD. What is required is a working understanding of the spirochete infection pathways involved and how best to reduce the opportunities for oral bacteria to travel to the brain to initiate the AD progression.

AD is an infectious and chronic disease with the involvement of the immune system in reaction to the establishment of biofilms from oral bacteria that have traveled to the brain from the oral cavity. Such bacteria then develop physical structures that initiate a parade of horribles in terms of how the body's immune system attempts to defeat a foe, all the while destroying the neural tissue surrounding the new biofilm and amyloid protected spirochetes. The destruction or dissolving of such biofilms has its own risks, as the achievement of such goal will result in the freeing of the infecting spirochete that causes the damage in the first place. Moreover, the adaptive immune system rapidly destroys brain tissue surrounding amyloid plaques, and explains why after the 30-odd years that it typically takes for AD to develop, it takes a mere 3 or so years for considerable damage to be done to a person's long infected brain. The older brains are different from younger brains in that such adaptive immune system responses are not permitted due to an intact blood brain barrier of younger individuals. Traumatic injuries to the brain tissue, however, permit immune responses to be observed in the brain. Support for this appreciation can be found in the NFL player's younger brains that have suffered repeated and violent trauma due to collisions and concussions. Such hemorrhagic cerebrovascular events like chronic traumatic encephalopathy (CTE) results in the formation of the amyloid structures seen in much older AD victims.

In terms of treatment, and as otherwise discussed herein, the provision of antibiotics effective against spirochetes is called for—with the caveat that they are administered early enough: e.g. prior to the establishment of protective biofilms such that the spirochetes cannot be killed. Penicillin administered before the disease starts is believed to be curative of AD and precludes it from taking its otherwise terrible path to destroy the mind.

Importantly, and again, not bound by theory, the present inventors believe that the rise in the occurrences of AD in the elderly populations has a correlation with dental practices that involve the bleeding of gums, thus presenting occasions where spirochetes can enter the blood stream and travel to the brain. Some have commented on the fact that while there have been very old individuals living in the US centuries ago, the number of AD cases has risen far faster than one would expect. The present inventors submit that the advent of modern dentistry, with wisdom tooth extractions, gum procedures, rough dental cleanings where blood is often a result, has unwittingly provided a path for the spirochetes resident in everyone's mouth to gain access to the blood stream, and thus the brain tissue, of millions of individuals in an unprecedented fashion. The more recent practice of providing antibiotics prior to or at the time of major dental procedures is a beneficial happening, but without a firm understanding of the causative factors of AD, protective procedures using antibiotics cannot be implemented in a thoughtful fashion to prevent the spread of AD.

As a practical matter, the infection (or re-infection) of a person's mouth with undesired bacteria is caused by the dental practices of individuals. For example, individual's toothbrush heads are typically contaminated as most people simply rinse the brush with plain tap water. Unfortunately, it is common for toothbrushes are routinely reused for months and sometimes for more than a year. The head of a toothbrush contains up to 100 million germs including many pathogenic bacteria that contribute to biofilm formations that lead to AD due to conveyance of spirochetes to brain tissue via the blood or nervous system pathways.

It is believed that because tooth brushing has become a universally accepted first line of defense against illness, and despite good intentions, the widespread practice of spreading spirochetes in the oral cavity and providing opportunities for them to enter the blood stream via disruption of the gums, causing bleeding thereof. In other words, while removal of pathogens from the mouth by toothbrush when used correctly has some benefits, it also leaves the toothbrush head contaminated as most people simply rinse the brush with plain tap water. In addition to bacteria and other microorganisms from the mouth, toothbrushes are often kept near dirty toilets and sinks, further increasing the possibility of contamination. Aerosols released after flushing the toilet have been shown to deliver fecal matter up to 20 feet in the air, reaching toothbrushes that have been stored on bathroom counters. It has been reported that toothbrushes could be a source of repeated oral infection.

Wisdom teeth have only become a problem in the last few centuries. Our jaws have gotten quite a bit smaller in response to the fact that we eat more processed and cooked foods than our ancestors did. In those older times when our jaws had begun to shrink, but not by so much as today, the teeth would get stuck, but not cause an infection or any biting problem much of the time. Moreover, unlike today—when wisdom teeth are routinely pulled even prior to wisdom teeth breaking the tissue surface, in olden days such wisdom teeth never did arise, and thus far fewer wisdom teeth extractions were seen. The first dentists did not graduate from a modern dental school until about 1870. Thus, the dental profession and the opportunities for an individual's gums to experience periodic and unprecedented trauma arose in tandem, and long with it, the rise in AD appeared from what was once an obscure condition. Alzheimer first diagnosed the disease in 1906 and Alzheimer died in 1915 at the age of 51—and had just two patients in his short lifetime that he reported as having the disease he is named for. Contrast this with the fact that Alzheimer's disease is currently ranked as the sixth leading cause of death in the United States, and recent estimates indicate that the disorder may rank third, just behind heart disease and cancer, as a leading cause of death for older people.

As further explained and described herein the provision of oral surfaces that inhibit the formation of undesired biofilms, whether used in concert with antibiotics or anti-biofilm agents or not, is another beneficial way in which to prevent the likelihood of AD progression. One objective of the present invention is to treat the conditions that result in the decades later development of AD—and such a temporal span makes it difficult to appreciate the benefits to be derived from sensible use of antibacterial structures, agents, etc. But if employed, the teachings of the present invention will assuredly significantly contribute to the future health of the next generation, such that the occurrence of AD can be expected to drop, and may eventually fade to its levels as seen in centuries past.

There is a significant association between spirochetes and Alzheimer's Disease. Spirochetes have been observed in the brain in more than 90% of Alzheimer's Disease cases. Various species of spirochetes are believed to contribute to AD, including the periodontal pathogens *Treponemas* (*T. pectinovorum, T. amylovorum, T. lecithinolyticum, T. maltophilum, T. medium, T. socranski*). Persisting inflammation and amyloid deposition initiated and sustained by chronic spirochetal infection results in the tragic progression of AD. Because spirochetal infection occurs years or decades before the manifestation of dementia, effective protocoals for antibiotic and anti-inflammatory therapies are required—and are described herein—such that AD, which like syphilis, is a spirochetes cased disease—can finally be avoided or at least reduced.

While the present application is primarily directed to AD, one of skill in the art will further appreciate that other disorders that are related to inflammatory diseases are also sought to be addressed by employing various systems and methods as disclosed herein. For example, atherosclerosis (AS) is a chronic disorder characterized by the formation and progression of plaques within arteries. Various microbes, most notably periodontal organisms, have been identified in plaques both epidemiologically and microbiologically, and the present inventors contend that they are contributors to the disease.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method of reducing the likelihood of a *Porphyromonas gingivalis* infection in a human being comprising,
providing to a human being who has been diagnosed with periodontitis, a therapeutically effective amount of a first composition comprising an anti-biofilm agent,
administering to the human being a second composition that is effective to either slow down the breakdown of collagen or inhibit the production of collagenase; and
orally administering to the subgingival tooth area of the human being a third composition comprising an antibiotic in an effective amount to kill *Porphyromonas gingivalis* bacteria residing on the subgingival tooth area of the human being, wherein the method reduces the likelihood of a *Porphyromonas gingivalis* infection in the human being and reduces the virulence factor gingipain.

2. The method as set forth in claim 1, further comprising administering to the human being a compound that facilitates the growth of desired bacteria beneficial to a person's health, said desired bacteria comprising one of a bacterium of the genus *Rothia*, a bacterium of species *Lactobacillus salivarius* and a bacterium of the species *Streptococcus salivarius*.

3. The method of claim 1, wherein said second composition is devoid of manganese.

4. The method of claim 1, wherein said second composition comprises an effective amount of paquinimod to inhibit collagenase activity.

5. The method as set forth in claim 1, wherein said second composition includes between 0.2 and 0.9% xylitol by weight.

6. The method as set forth in claim 1, wherein said antibiotic comprises one of azithromycin, metronidazole and ceftriaxone.

7. The method as set forth in claim 1, further comprising administering to the human being *Porphyromonas gingivalis* that has been modified by using a clustered regularly interspaced short palindromic repeat (CRISPR) CRISPR associated protein (Cas) system, or a CRISPR/Cpf1 system, to reduce the virulence factor gingipain.

8. The method as set forth in claim 1, wherein administration of the second composition is provided in the form of one of a toothpaste, a mouthwash, a chewing gum, a thin film strip, a lozenge, a dental floss, a food product, a gel, and a slow-release gel.

9. The method as set forth in claim 1, wherein the second composition produces nitric oxide.

10. The method as set forth in claim 1, wherein the second composition includes zinc or zinc salts.

11. The method as set forth in claim 1, further comprising reducing the amount of *F. nucleatum* in the human being's oral cavity.

12. The method as set forth in claim 1, further comprising providing the oral cavity of the human being with bacteria that have had one or more virulence factors eliminated to reduce adherence abilities of such bacteria in forming biofilms.

13. The method as set forth in claim 1, the antibiotic is provided in an effective amount to kill spirochetes bacteria.

14. The method as set forth in claim 1, wherein the oral environment of the human being is adjusted to have a pH of lower than 6.5.

15. A method of reducing the likelihood of a *Porphyromonas gingivalis* infection in a human being comprising,
orally administering to a human being a first composition comprising an anti-biofilm agent, said anti-biofilm agent comprising a mouthwash, an oral strip or toothpaste;
administering to the human being a second composition that is effective to one of slow down the breakdown of collagen or inhibit the production of collagenase;
orally administering to the human being a third composition in an effective amount to reduce the growth of *Porphyromonas gingivalis* bacteria residing on the subgingival tooth area of the human being, wherein the method reduces the likelihood of a *Porphyromonas gingivalis* infection in the human being and reduces the virulence factor gingipain.

16. The method as set forth in claim 15, further comprising administering to the human being a compound that facilitates the growth of desired bacteria beneficial to a person's health, said desired bacteria comprising one of a bacterium of the genus *Rothia*, and a bacterium of the species *Streptococcus salivarius*.

17. The method as set forth in claim 15, further comprising orally administering an antibiotic that comprises one of azithromycin, metronidazole and ceftriaxone.

18. The method as set forth in claim 15, further comprising reducing the amount of *F. nucleatum* in the human being's oral cavity.

19. A method of reducing the likelihood of a *Porphyromonas gingivalis* infection in a human being comprising,
adjusting the oral cavity pH of the human being to have a pH of lower than 6.5;
reducing the amount of *Fusobacterium nucleatum* in the human being's oral cavity;
orally administering to a human being a first composition comprising an anti-biofilm agent,
orally administering to the human being a second composition that is effective to one of slow down the breakdown of collagen or inhibit the production of collagenase, said second composition including at least about 200 mg xylitol,
orally administering to the human being zinc or a nontoxic zinc salt;
orally administering to the human being a third composition in an effective amount to reduce the growth of *Porphyromonas gingivalis* bacteria residing on the subgingival tooth area of the human being, wherein the method reduces the likelihood of a *Porphyromonas gingivalis* infection in the human being and reduces the virulence factor gingipain, and
wherein said anti-biofilm agent, said second composition and said third composition comprise one of a mouthwash, an oral strip and toothpaste.

20. The method as set forth in claim 19, further comprising administering to the human being a compound that facilitates the growth of desired bacteria beneficial to a person's health, said desired bacteria comprising a bacterium of the genus *Rothia*.

* * * * *